US009179984B2

(12) United States Patent
Teichman et al.

(10) Patent No.: US 9,179,984 B2
(45) Date of Patent: Nov. 10, 2015

(54) MULTI-CONFIGURATION TRACKING ARRAY AND RELATED METHOD

(75) Inventors: Robert Teichman, Lafayette, CO (US); David Mire, Cordova, TN (US); Jason Tipton, Westminster, CO (US); Steven L. Hartmann, Superior, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1540 days.

(21) Appl. No.: 11/708,152

(22) Filed: Feb. 19, 2007

(65) Prior Publication Data

US 2008/0200794 A1 Aug. 21, 2008

(51) Int. Cl.
*A61B 5/05* (2006.01)
*A61B 19/00* (2006.01)
*A61B 17/00* (2006.01)

(52) U.S. Cl.
CPC ............. *A61B 19/5244* (2013.01); *A61B 19/54* (2013.01); *A61B 2017/00477* (2013.01); *A61B 2019/505* (2013.01); *A61B 2019/508* (2013.01); *A61B 2019/5238* (2013.01); *A61B 2019/5251* (2013.01); *A61B 2019/5255* (2013.01); *A61B 2019/5291* (2013.01); *A61B 2019/5483* (2013.01); *A61B 2019/566* (2013.01)

(58) Field of Classification Search
CPC ............... A61B 19/5244; A61B 19/54; A61B 2017/00477; A61B 2019/505; A61B 2019/508; A61B 2019/5238; A61B 2019/5251; A61B 2019/5255; A61B 2019/5291; A61B 2019/5483; A61B 2019/566
USPC ......... 600/407, 409, 410, 411, 424–429, 437, 600/473, 476
See application file for complete search history.

(56) References Cited

U.S. PATENT DOCUMENTS

| 4,705,038 A | 11/1987 | Sjostrom et al. |
| 5,442,082 A | 8/1995 | Uphues et al. |
| 5,610,811 A | 3/1997 | Honda et al. |
| 5,740,808 A | 4/1998 | Panescu et al. |

(Continued)

FOREIGN PATENT DOCUMENTS

| DE | 10239710 | 3/2004 |
| EP | 1518508 | 3/2005 |

(Continued)

OTHER PUBLICATIONS

"Chips are just what the doctor ordered", article dated Nov. 14, 2006, The Sydney Morning Herald, http://www.smh.com.au/articles/2006/11/13/1163266481840.html?page=fullpage, printed Dec. 11, 2006 (2 pgs).

(Continued)

*Primary Examiner* — Mark Remaly
(74) *Attorney, Agent, or Firm* — Harness, Dickey

(57) ABSTRACT

A navigation system generally determines a location of a portion of a first medical instrument relative to a patient. The navigation system generally includes a multi-configuration tracking array that extends from the first medical instrument. A plurality of tracking devices can be positioned on the multi-configuration tracking array. At least one of the tracking devices changes to define at least a first condition and a second condition. A tracking system detects the tracking devices and relates a change between the first condition and the second condition with a change between at least a first instrument configuration and a second instrument configuration.

52 Claims, 11 Drawing Sheets

(56) References Cited

U.S. PATENT DOCUMENTS

| | | | |
|---|---|---|---|
| 6,226,548 B1 | 5/2001 | Foley et al. | |
| 6,264,647 B1 | 7/2001 | Lechot et al. | |
| 6,381,485 B1 | 4/2002 | Hunter et al. | |
| 6,434,507 B1 | 8/2002 | Clayton et al. | |
| 6,540,739 B2 | 4/2003 | Lechot et al. | |
| 6,689,138 B2 | 2/2004 | Lechot et al. | |
| 6,861,954 B2 | 3/2005 | Levin | |
| 6,891,475 B2 | 5/2005 | Bui et al. | |
| 6,925,339 B2 * | 8/2005 | Grimm et al. | 700/59 |
| 7,005,968 B1 | 2/2006 | Bridgelall | |
| 7,567,834 B2 | 7/2009 | Clayton et al. | |
| 8,233,963 B2 | 7/2012 | Hartmann et al. | |
| 8,600,478 B2 | 12/2013 | Verard et al. | |
| 2002/0032380 A1 | 3/2002 | Acker et al. | |
| 2004/0215071 A1 | 10/2004 | Frank et al. | |
| 2004/0267297 A1 | 12/2004 | Malackowski | |
| 2005/0041966 A1 * | 2/2005 | Johnson | 396/428 |
| 2005/0085714 A1 * | 4/2005 | Foley et al. | 600/424 |
| 2005/0085720 A1 | 4/2005 | Jascob et al. | |
| 2005/0215888 A1 | 9/2005 | Grimm et al. | |
| 2006/0029186 A1 * | 2/2006 | De Villiers et al. | 378/163 |
| 2006/0043179 A1 | 3/2006 | Nycz et al. | |
| 2006/0055712 A1 | 3/2006 | Anderson | |
| 2006/0094958 A1 | 5/2006 | Marquart et al. | |
| 2006/0142656 A1 | 6/2006 | Malackowski et al. | |
| 2006/0161059 A1 | 7/2006 | Wilson | |
| 2006/0173291 A1 | 8/2006 | Glossop | |
| 2006/0184396 A1 | 8/2006 | Dennis et al. | |
| 2006/0264742 A1 | 11/2006 | Neubauer et al. | |
| 2007/0016009 A1 | 1/2007 | Lakin et al. | |
| 2007/0249901 A1 | 10/2007 | Ohline et al. | |
| 2008/0200926 A1 | 8/2008 | Verard et al. | |
| 2008/0200927 A1 | 8/2008 | Hartmann et al. | |
| 2012/0296203 A1 | 11/2012 | Hartmann et al. | |
| 2014/0081128 A1 | 3/2014 | Verard et al. | |

FOREIGN PATENT DOCUMENTS

| | | |
|---|---|---|
| EP | 1719472 | 11/2006 |
| EP | 2124796 A1 | 12/2009 |
| WO | WO-2008103266 A1 | 8/2008 |

OTHER PUBLICATIONS

Hoff, et al., Automatic Tool Identification and Registration, Colorado School of Mines, Feb. 26, 2005 (8 pages).

International Search Report and Written Opinion for PCT/US2008/001977 mailed Sep. 16, 2008 claiming benefit of U.S. Appl. No. 11/708,152, filed Feb. 19, 2007.

International Search Report and Written Opinion for PCT/US2008/001992 mailed Aug. 12, 2008 claiming benefit of U.S. Appl. No. 11/708,159, filed Feb. 19, 2007.

International Search Report and Written Opinion mailed Jun. 17, 2008 for PCT/US2008/001947.

Kiefer, Automatic Recognition of Medical Instruments, Using MATLAB to recognize medical tools with the use of fiducial markings, EGES510: Multidimensional Signal and Image Processing Final Project, Dec. 12, 2005 (19 pages).

L10-USB-Pen Reader, RFID 125 KHz, Part Nr 205 0014, data sheet, Version 1.02, MBBS S.A., 2005 (1 pg).

L10-USB-Tray Reader, RFID 125 KHz, Part Nr 200 0016, data sheet, Version 1.02, MBBS S.A., 2005 (1 pg).

MediTAG™ metal 8.0, RFID 125 KHz, 2K Read/Write, Part Nr 103 0003, data sheet, Version 1.02, MBBS S.A., 2005 (1 pg).

MediTAG™ plastic 5.6, RFID 125 KHz, 2K Read/Write, Part Nr 105 0051, datasheet, Version 1.03, MBBS S.A., 2005 (1 pg).

MediTAG™ tray 70×40, RFID 125 KHz, 2K Read/Write, Part Nr 105 0059, data sheet, Version 1.03, MBBS S.A., 2005 (1 pg).

RFID, Information at the Surgeon's Fingertips, brochure, Precimed SA and MBBS SA, 2005 (6 pgs).

International Preliminary Report on Patentability and Written Opinion mailed Aug. 19, 2009 for PCT/US2008/001947 claiming benefit of U.S. Appl. No. 11/708,157, filed Feb. 19, 2007.

International Preliminary Report on Patentability and Written Opinion mailed Aug. 27, 2009 for PCT/US2008/001977 claiming benefit of U.S. Appl. No. 11/708,152, filed Feb. 19, 2007.

International Preliminary Report on Patentability and Written Opinion mailed Aug. 27, 2009 for PCT/US2008/001992 claiming benefit of U.S. Appl. No. 11/708,159, filed Feb. 19, 2007.

* cited by examiner

MULTI-CONFIGURATION TRACKING ARRAY AND RELATED METHOD

CROSS-REFERENCE TO RELATED APPLICATIONS

This application is filed concurrently with U.S. patent application Ser. No. 11/708,157 entitled, "AUTOMATIC IDENTIFICATION OF INSTRUMENTS USED WITH A SURGICAL NAVIGATION SYSTEM"; and U.S. patent application Ser. No. 11/708,159 entitled, "AUTOMATIC IDENTIFICATION OF TRACKED SURGICAL DEVICES USING AN ELECTROMAGNETIC LOCALIZATION SYSTEM." The disclosures of the above applications are incorporated herein by reference.

FIELD

The present teachings relate to a surgical navigation system and more particularly relate to a multi-configuration tracking array that can indicate a change in an instrument configuration.

BACKGROUND

The statements in this section merely provide background information related to the present disclosure and may not constitute prior art.

Image guided medical and surgical procedures utilize patient images obtained prior to or during a medical procedure to guide a physician performing the procedure. Such procedures can be referred to as computer assisted procedures. Recent advances in imaging technology, especially in imaging technologies that produce highly-detailed, two, three, and four dimensional images, such as computed tomography (CT), magnetic resonance imaging (MRI), fluoroscopic imaging (such as with a C-arm device), positron emission tomography (PET), and ultrasound imaging (US) has increased the interest in image guided medical procedures.

Typical image guided navigation systems require a dynamic reference frame to track the position of the patient when patient movement occurs during the assisted procedure. The dynamic reference frame is generally affixed to the patient in a generally permanent or immovable fashion. The dynamic reference frame may also be used as a fiducial marker and may, therefore, be attached to the patient during the acquisition of pre-operative images. This enables the image space to be aligned with patient space during the navigated procedure.

Various instruments that are desired to be tracked may be used during an operative procedure. Image data is generally acquired, either intra-operatively or pre-operatively, and the instrument is generally illustrated, and superimposed on the captured image data to identify the position of the instrument relative to the patient space. Therefore, the instrument may include tracking sensors, such as electromagnetic coils or optical detection points, such as light emitting diodes or reflectors that may be detected by a suitable tracking system. Also, the dynamic reference frame (DRF) can be used by the tracking system to maintain a registration or localization of the patient space to the image space. The DRF can also include any appropriate tracking sensor that is fixed to a portion of the patient that allows the system to determine whether the patient has moved relative to the image space.

Other types of navigation systems operate as an image-less system, where an image of the body is not captured by an imaging device prior to the medical procedure, such as the device disclosed in U.S. patent application Ser. No. 10/687,539, entitled Method and Apparatus for Surgical Navigation of a Multiple Piece Construct For Implantation, filed Oct. 16, 2003, which is hereby incorporated by reference as if fully set forth herein. With this type of procedure, the system may use a probe to contact certain landmarks in the body, such as landmarks on bone, where the system generates either a two-dimensional or a three-dimensional model of the area of interest based upon these contacts. This way, when the surgical instrument or other object is tracked relative to this area, they can be superimposed on this model.

During surgical navigation, image data of the patient can be correlated with the architecture of various surgical instruments. Typically, each instrument is registered with the surgical navigation system so that when the surgical navigation system detects the instrument, the registration and the architecture of the instrument are matched. During a procedure, however, the medical professional may need to change the orientation of the instrument, his or her orientation relative to the instrument and/or add or remove components to/from the instrument during the procedure. Typically, each of the above changes to the instrument requires an additional registration so that the new instrument configuration is registered with the surgical navigation system.

For example, certain instruments can receive additional components during a medical procedure. The instrument can have a first configuration that defines a bare instrument, i.e., no additional components attached to the instrument. The first configuration can be stored in the surgical navigation system. A component can be added to the instrument, which requires a re-registration so the architecture of the component in addition to the architecture of the instrument is registered with the surgical navigation system. It will be appreciated that as each configuration of the instrument changes, the instrument's new configuration must be re-registered. While the above devices and methods remain useful for their intended purpose there remains room in the art for improvement.

SUMMARY

The present teachings generally include a navigation system that determines a location of a portion of a first medical instrument relative to a patient. The navigation system generally includes a multi-configuration tracking array that extends from the first medical instrument. A plurality of tracking devices can be positioned on the multi-configuration tracking array. At least one of the tracking devices changes to define at least a first condition and a second condition. A tracking system detects the tracking devices and relates a change between the first condition and the second condition with a change between at least a first instrument configuration and a second instrument configuration.

Further areas of applicability will become apparent from the description provided herein. It should be understood that the description and specific examples are intended for purposes of illustration only and are not intended to limit the scope of the present teachings.

DRAWINGS

The present teachings will become more fully understood from the detailed description, the appended Claims and the following drawings, each of which are briefly described below.

Figure 10:
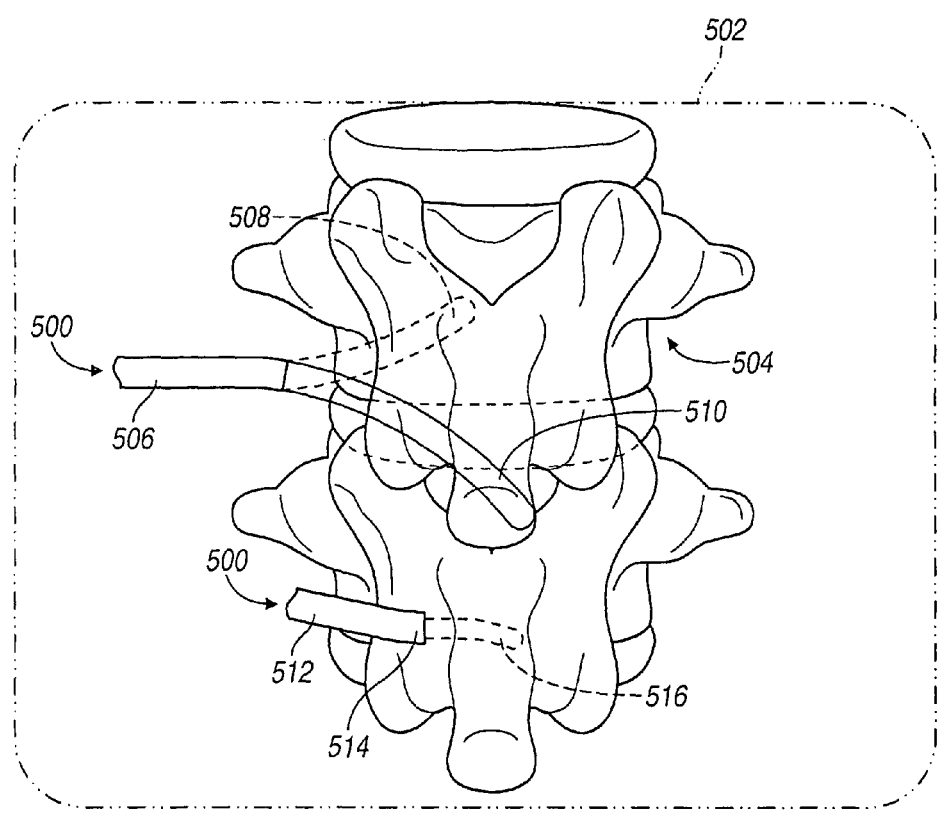

FIG. 10 is a diagram showing a first icon and a second icon over image data of patient anatomy so that the change between the first icon and the second icon indicates the change between the first condition and the second condition of the multi-configuration tracking array that indicates a change between the first instrument configuration and the second instrument configuration as represented in the icons in accordance with the present teachings.

Figure 11:
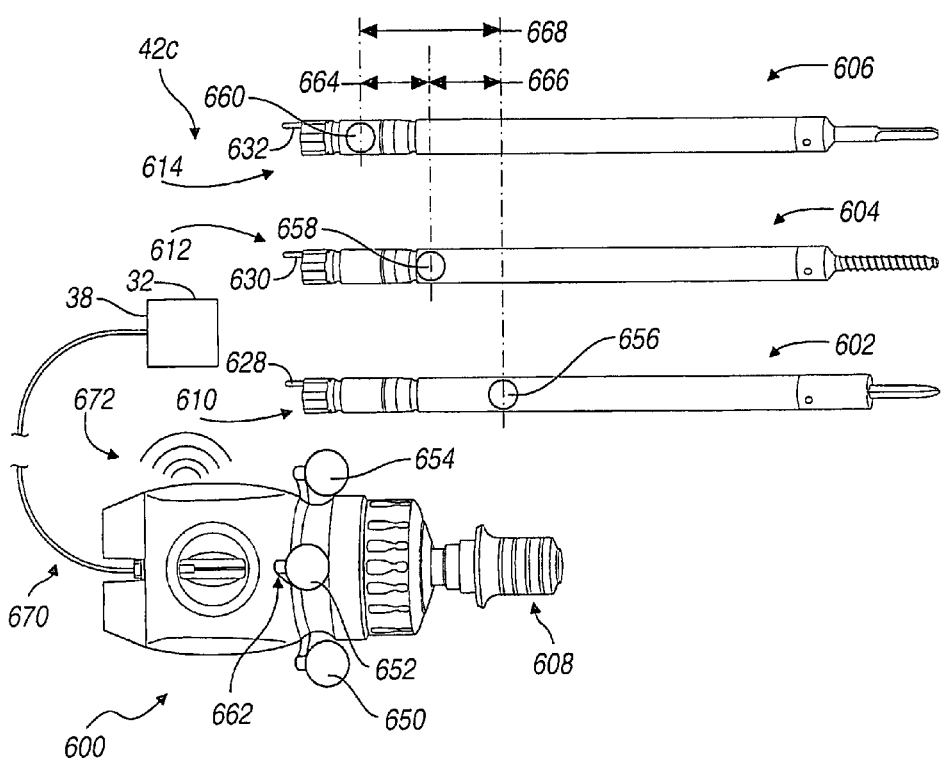

FIG. 11 is a diagram of a multi-tip tool having tracking devices associated with a handle portion and selectable tip portions that can establish an alternative example of a multi-configuration tracking array that can be used to detect the different tip portions that can be connected to the handle portion in accordance with various aspects of the present teachings.

DETAILED DESCRIPTION

The following description is merely exemplary in nature and is not intended to limit the present teachings, their application, or uses. It should be understood that throughout the drawings, corresponding reference numerals indicate like or corresponding parts and features.

In addition, certain terminology can be used for the purpose of reference only and do not limit the present teachings. For example, terms such as "upper," "lower," "above" and "below" can refer to directions in the drawings to which reference is made. Terms such as "front," "back," "rear" and "side" can describe the orientation of portions of the component within a consistent but arbitrary frame of reference which can be made more clear by reference to the text and the associated drawings describing the component under discussion. Such terminology may include the words specifically mentioned above, derivatives thereof and words of similar import. Similarly, the terms "first," "second" and other such numerical terms referring to structures, systems and/or methods do not imply a sequence or order unless clearly indicated by the context.

The present teachings generally include a method and an apparatus to perform a procedure that can include a processor assisted surgical procedure. During the procedure, a patient space and an image space can be registered to allow for tracking of various tracking devices. A dynamic reference frame can be selectively interconnected with a portion of the anatomy to maintain localization of the patient space with the image space. Although the following description describes the use of a dynamic reference frame positioning member in relation to a pelvis, it will be appreciated in light of the disclosure that the dynamic reference frame can be positioned in any portion of the anatomy. Further, the dynamic reference frame can be used for an orthopedic procedure, a spinal procedure, a neural procedure, a cardiac procedure or any other surgical or medical procedure.

Figure 1:
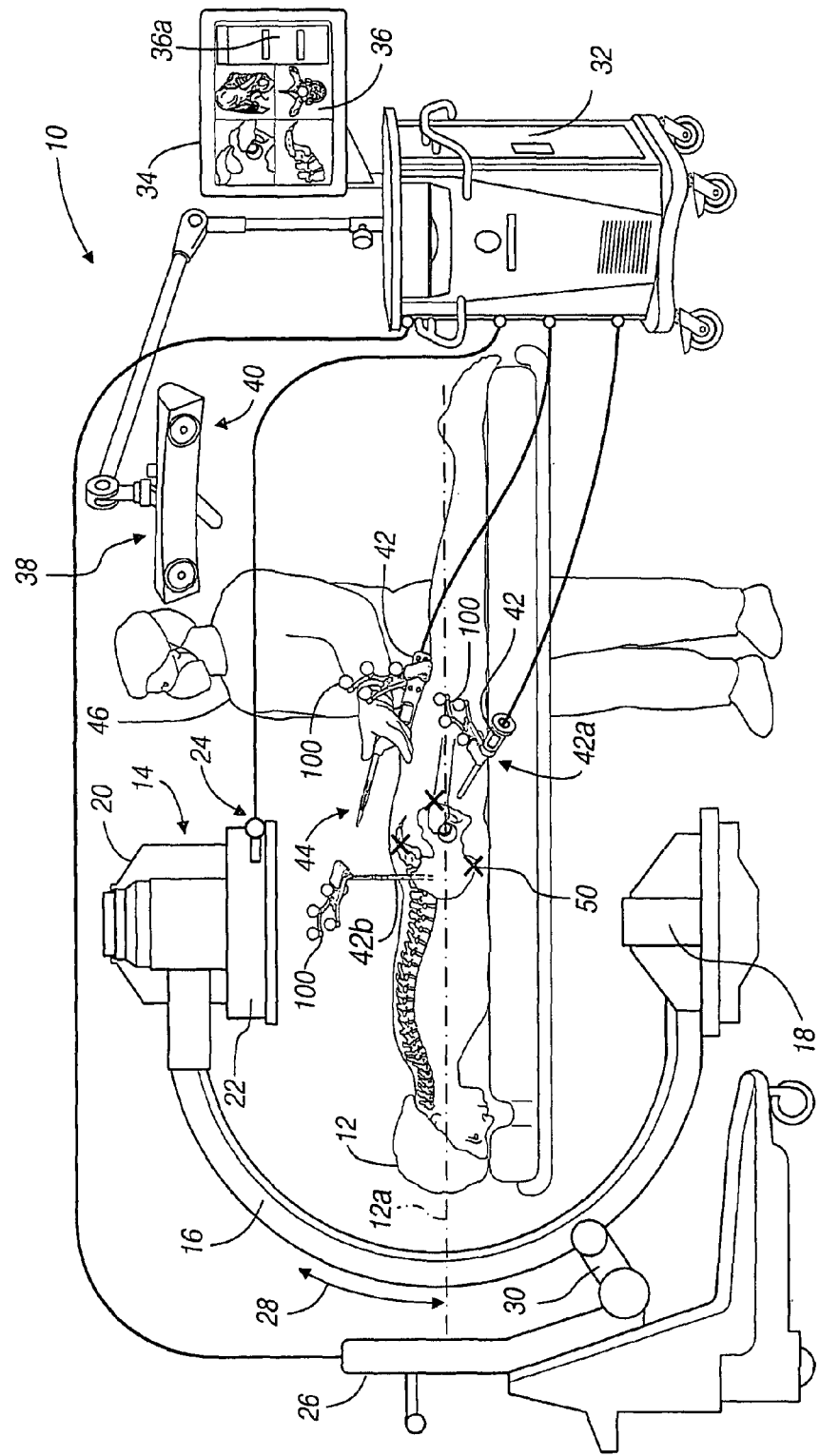
FIG. 1 is a diagram of an exemplary surgical navigation system having a detector that can track an instrument to be used with a medical procedure in accordance with various aspects of the present teachings.

FIG. 1 is a diagram illustrating an overview of an image-guided surgical navigation system 10 that can be used for various procedures. The navigation system 10 can be used to track the location of an implant, such as a spinal implant or orthopedic implant, relative to a patient 12. Also the navigation system 10 can track the position and orientation of various instruments. The navigation system 10 can also be used to navigate any type of instrument, implant or delivery system, including: guide wires, arthroscopic systems, orthopedic implants, spinal implants, deep brain stimulation probes, etc. Moreover, these instruments can be used to navigate or map any region of the body. The navigation system 10 and the various instruments can be used in any appropriate procedure, such as one that is generally minimally invasive or an open procedure.

Figure 2:
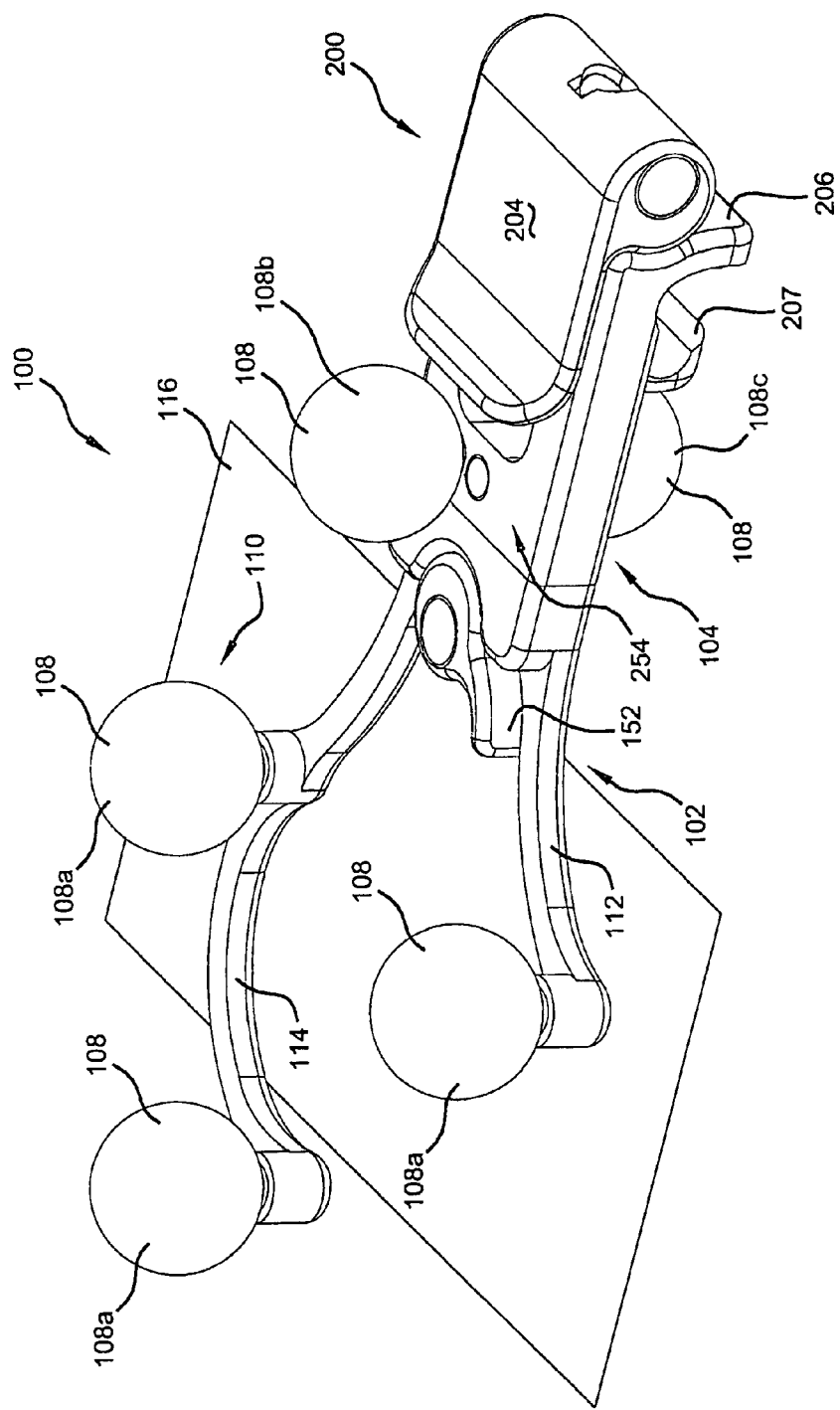
FIG. 2 is a perspective view of a multi-configuration tracking array that can attach to an instrument so that the surgical navigation system can track the instrument in accordance with various aspects of the present teachings.
Figure 3:
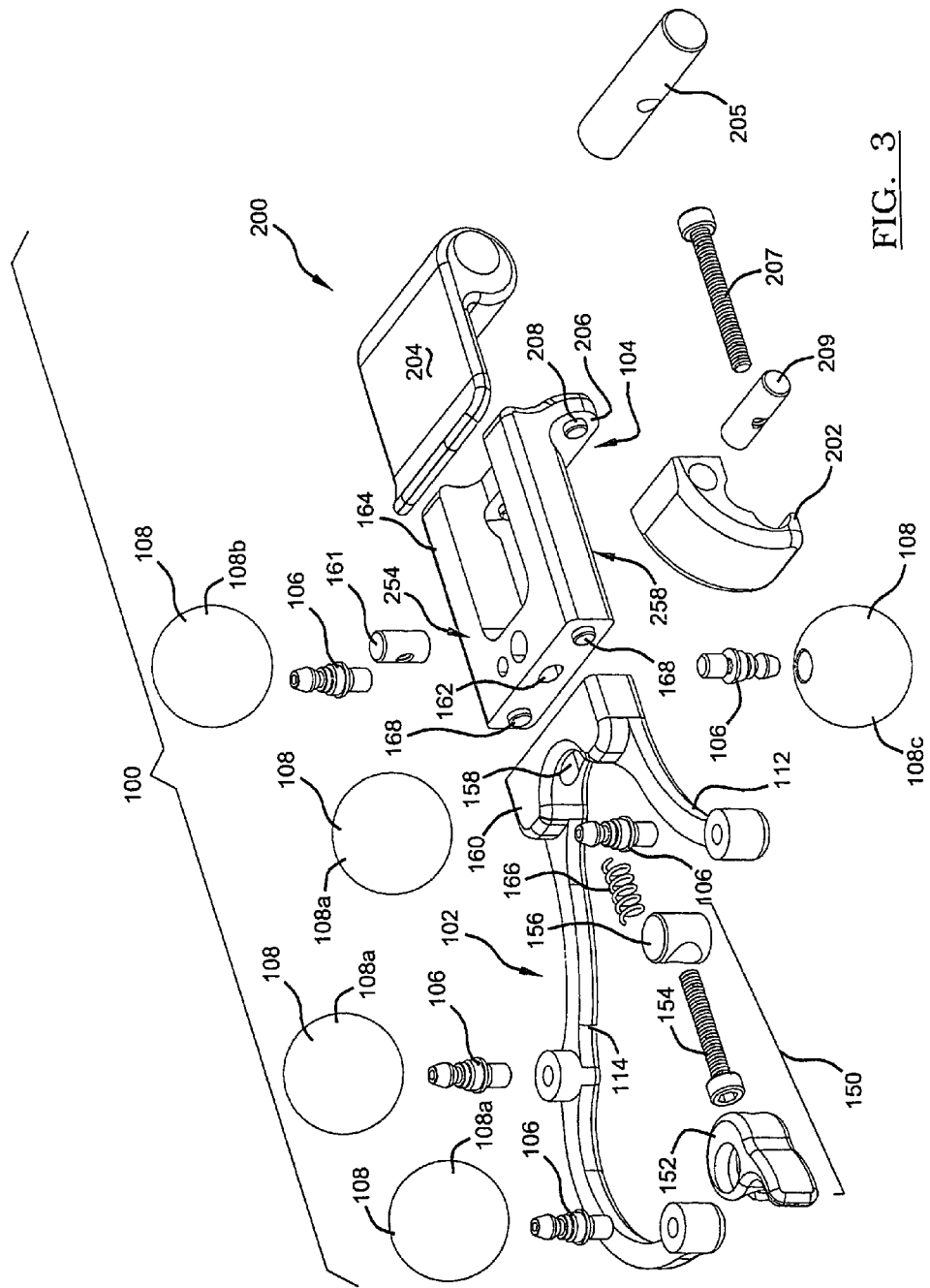
FIG. 3 is an exploded assembly view of the multi-configuration tracking array of FIG. 2 showing a tracking device holder member and an instrument holder member constructed in accordance with various aspects of the present teachings.

In accordance with the various aspects of the present teachings and with reference to FIGS. 2 and 3, a multi-configuration tracking array 100 can be used with the navigation system 10 (FIG. 1) to track one or more of the instruments used during a medical process. The multi-configuration tracking array 100 can include a tracking device holder member 102 and an instrument holder member 104. A plurality of posts 106 can each extend from various locations on the tracking device holder member 102 and/or the instrument holder member 104. Each of the posts 106 can couple to a tracking device 108. The navigation system 10 can detect changes in configuration to the tracking devices 108 and based on the changes to the tracking devices 108, the navigation system 10 can relate the changes as a change in an instrument configuration, which is provided in further detail herein.

The navigation system 10 can include an imaging device 14 that is used to acquire pre-, intra-, or post-operative or real-time image data of the patient 12. Alternatively various imageless systems can be used or images from atlas models can be used to produce patient images. In this regard, known anatomical atlas maps may be used and scaled to a particular patient or patient specific atlas maps can also be used. These atlas maps and/or patient specific atlas maps can be superimposed onto patient image data to identify relevant locations of the anatomy. Suitable imageless systems can include, for example, those disclosed in U.S. Patent Publication Number 2005/0085714, filed Oct. 16, 2003, entitled Method and Apparatus for Surgical Navigation of a Multiple Piece Construct for Implantation, which is hereby incorporated by reference as if fully set forth herein. The imaging device 14 can be, for example, a fluoroscopic x-ray imaging device that can be configured as an O-arm™ or a C-arm 16 having an x-ray source 18, an x-ray receiving section 20, an optional calibration and tracking target 22 and optional radiation sensors 24.

Image data can also be acquired using other imaging devices, such as those discussed above and herein. An imaging device controller 26 that can control the C-arm 16 can capture the x-ray images received at the receiving section 20 and store the images for later use. The controller 26 can also be separate from the C-arm 16 and/or control the rotation of the C-arm 16. For example, the C-arm 16 can move in the direction of arrow 28 or rotate about a longitudinal axis 12*a* of the patient 12, allowing various anatomical views of the patient 12 to be imaged. Each of these movements involves rotation about a mechanical axis 30 of the C-arm 16.

In the example of FIG. 1, the longitudinal axis 12*a* of the patient 12 can be substantially in line with the mechanical axis 30 of the C-arm 16. This can enable the C-arm 16 to be rotated relative to the patient 12, allowing images of the patient 12 to be taken from multiple directions or about multiple planes. An example of a fluoroscopic C-arm x-ray device that can be used as the imaging device 14 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc. An exemplary O-arm™ imaging device is available from Breakaway Imaging, LLC of Littleton, Mass.

In operation, the imaging device 14 generates x-rays from the x-ray source 18 that propagate through the patient 12 and the calibration and/or tracking target 22, into the x-ray receiving section 20. It will be appreciated in light of the disclosure that the tracking target 22 need not include a calibration portion. The receiving section 20 generates image data representing the intensities of the received x-rays. Typically, the receiving section 20 includes an image intensifier that first converts the x-rays to visible light and a charge coupled device (CCD) video camera that converts the visible light into digital image data.

Receiving section 20 can also be a digital device that converts x-rays directly to digital image data for forming images, thus potentially avoiding distortion introduced by first converting to visible light. Alternatively, the imaging device 14 can only take a single image with the calibration and tracking target 22 in place. Thereafter, the calibration and tracking target 22 can be removed from the line-of-sight of the imaging device 14. When the x-ray source 18 generates the x-rays that propagate to the x-ray receiving section 20, the radiation sensors 24 sense the presence of radiation, which can be forwarded to the controller 26, to identify whether or not the imaging device 14 is actively imaging.

Two dimensional fluoroscopic images that can be taken by the imaging device 14 can be captured and stored in the controller 26. Multiple two-dimensional images taken by the imaging device 14 can also be captured and assembled to provide a larger view or image of a whole region of a patient, as opposed to being directed to only a portion of a region of the patient 12. For example, multiple image data of a patient's leg can be appended together to provide a full view or complete set of image data of the leg that can be later used to follow a contrast agent, such as Bolus tracking.

The image data is then forwarded from the controller 26 to a navigation computer and/or processor, controller or workstation 32 having a display 34 and a user interface 36. It will be appreciated in light of the disclosure that the image data is not necessarily first retained in the controller 26, but can also be directly transmitted to the workstation 32. The workstation 32 can provide facilities for displaying the image data as an image on the display 34, saving, digitally manipulating, or printing a hard copy image of the received image data. The user interface 36 can comprise any device, such as a user input device 36*a*, that can enable a user to interface with the workstation 32, such as a touchpad, touch pen, touch screen, keyboard, mouse, wireless mouse, or a combination thereof. The user interface 36 allows a physician or user to control the navigated surgical procedure.

While the imaging device 14 is shown in FIG. 1, any other alternative 2D, 3D or 4D imaging modality can also be used. For example, any 2D, 3D or 4D imaging device, such as an O-arm imaging device, isocentric fluoroscopy, bi-plane fluoroscopy, ultrasound, computed tomography (CT), multi-slice computed tomography (MSCT), magnetic resonance imaging (MRI), high frequency ultrasound (HFU), positron emission tomography (PET), optical coherence tomography (OCT), intra-vascular ultrasound (IVUS), ultrasound, intra-operative CT or MRI can also be used to acquire 2D, 3D or 4D pre- or post-operative and/or real-time images or image data of the patient 12. The images can also be obtained and displayed in two, three or four dimensions. In more advanced forms, four-dimensional surface rendering regions of the body can also be achieved by incorporating patient data or other data from an atlas or anatomical model map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems and Methods For Guiding Diagnostic or Therapeutic Devices in Interior Tissue Regions" which is hereby incorporated by reference as if fully set forth herein.

Image datasets from hybrid modalities, such as positron emission tomography (PET) combined with CT, or single photon emission computer tomography (SPECT) combined with CT, could also provide functional image data superimposed onto anatomical data to be used to confidently reach target sites within the patient 12. It should further be noted that the imaging device 14, as shown in FIG. 1, provides a virtual bi-plane image using a single-head C-arm fluoroscope as the imaging device 14 by simply rotating the C-arm 16 about at least two planes, which could be orthogonal planes to generate two-dimensional images that can be converted to three-dimensional volumetric images. By acquiring images in more than one plane, an icon representing the location of an impacter, stylet, reamer driver, taps, drill, or other instrument, introduced and advanced in the patient 12, can be superimposed in more than one view on display 34 allowing simulated bi-plane or even multi-plane views, including two and three-dimensional views, as will be discussed in greater detail herein.

With continuing reference to FIG. 1, if the navigation system 10 is a line-of-sight system, the navigation system 10 can further include an optical tracking system 38. The tracking system 38 can include a camera 40 and the multi-configuration tracking array 100 or other suitable tracking arrays that can be attached to various instruments or implants 42. The camera 40 can be an optical localizer such as that used in the StealthStation® TRIA™ sold by Medtronic Navigation of Louisville, Colo. The instruments 42 can include an instrument 42*a* for use in the procedure and a dynamic reference frame or DRF 42*b*. Each of the instruments 42 can include either a passive or an active reflective multi-configuration tracking array 100 that can be attached to the instruments 42, and can include the tracking devices 108 as will be discussed in greater detail herein. The optical tracking system 38 is generally considered a line-of-sight tracking system because the tracking devices 108 connected to the instruments 42 are tracked based on their optical visibility to the camera 40.

The instrument 42 can be any appropriate instrument, such as an instrument for preparing a portion of the patient or positioning an implant. The instrument 42 can also be a handle or inserter that interconnects with an attachment and can assist in placing an implant or in driving a portion. The instrument 42 can include a graspable or manipulable portion at a proximal end and the multi-configuration tracking array 100 can be fixed near the manipulable portion of the instrument 42, as will be discussed in greater detail herein. The DRF 42b can be fixed to the patient 12 adjacent to the region being navigated so that any movement of the patient 12 is detected. The DRF 42b can include any appropriate tracking device or array, such as the multi-configuration tracking array 100, recognized by the navigation system 10.

Briefly, the navigation system 10 operates as follows. The navigation system 10 can create a translation map between all points in the radiological image generated from the imaging device 14 and the corresponding points in the patient's anatomy in patient space. After this map is established, whenever a tracked instrument, such as the instrument 42 or a pointing device or probe 44 is used, the workstation 32 in combination with the tracking system 38 and the controller 26 can use the translation map to identify the corresponding point on the pre-acquired image or atlas model, which is displayed on display 34. This identification is known as navigation or localization. An icon representing the localized point or instruments can be shown on the user interface 36 within several two-dimensional image planes, as well as on three and four dimensional images and models, as will be discussed herein.

To enable navigation, the navigation system 10 must be able to detect both the position of the patient's anatomy and the position of the instrument 42 or attachment member attached to the instrument 42a. Knowing the location of these two items can allow the navigation system 10 to compute and display the position of the instrument 42 in relation to the patient 12. The tracking system 38 can be employed to track the instrument 42 and the anatomy simultaneously.

The tracking system 38 essentially works by using the camera 40 adjacent to the patient space to generate a visual field, referred to as a navigation field. The DRF 42b can be fixed to the patient 12 to identify the location of the patient 12 in the navigation field. The tracking system 38 can continuously re-compute the relative position of the DRF 42b and the instrument 42a during localization and relates this spatial information to patient registration data to enable image guidance of the instrument 42 within and/or relative to the patient 12.

Many different forms and methods of the patient registration can be used with the navigation system 10, such as U.S. Pat. No. 6,226,548, entitled "Percutaneous Registration Apparatus and Method for use in Computer-Assisted Surgical Navigation," issued May 1, 2001 and U.S. Pat. No. 6,381,485, entitled "Registration of Human Anatomy Integrated for Electromagnetic Localization," issued Apr. 30, 2002, which are hereby incorporated by reference as if fully set forth herein.

The navigation system 10 can also perform registration using anatomic surface information or path information as is known in the art. The navigation system 10 can also perform 2D to 3D registration by utilizing the acquired 2D images to register 3D volume images by use of contour algorithms, point algorithms or density comparison algorithms, as is known in the art. An exemplary 2D to 3D registration procedure, is set forth in U.S. Ser. No. 60/465,615, entitled "Method and Apparatus for Performing 2D to 3D Registration" filed on Apr. 25, 2003, which is hereby incorporated by reference as if fully set forth herein.

The navigation system 10 can be used according to any appropriate method or system. For example, pre-acquired images, atlas or 3D models can be registered relative to the patient and patient space. Generally, the navigation system 10 allows the images on the user interface 36 to be registered and to accurately display the real time location of the various instruments 42 and other suitable items. In addition, the DRF 42b can be used to ensure that any planned or unplanned movement of the patient is determined and used to correct the image on the display 34.

It will be appreciated in light of the disclosure that the tracking system employed with the navigation system 10 can also be a hybrid tracking system, and can include both optical and electromagnetic (EM) tracking system components. Further detail regarding the EM tracking system is outside the scope of the present disclosure but is disclosed in greater detail in U.S. patent application Ser. No. 10/941,782, filed Sep. 15, 2004, and entitled "Method and Apparatus for Surgical Navigation," hereby incorporated by reference as if fully set forth herein. Further, other tracking systems could be employed with the tracking system 38 for use by the navigation system 10, such as an acoustic, radiation, etc.

With reference to FIGS. 1 and 2, the multi-configuration tracking array 100 including the tracking devices 108 can enable the instrument 42a and, optionally, the DRF 42b to be located by the camera 40. In this regard, the tracking devices 108 on the multi-configuration tracking array 100 can provide a signal, such as a reflection or an emission of infrared (IR) light, which is visible or recognizable by the camera 40. The camera 40 can then transmit this image or signal to the workstation 32. The workstation 32 can then locate the instrument 42a and/or the DRF 42b relative to the patient 12 based on the signal received by the camera 40 from the tracking devices 108. The multi-configuration tracking array 100 can employ at least three tracking devices 108 to enable the determination of the position and the orientation of the instrument 42 in six degrees of freedom.

In accordance with the various aspects of the present teachings and with reference to FIGS. 2 and 3, the multi-configuration tracking array 100 can include the tracking devices 108 that can communicate (actively and/or passively) with the optical tracking system 38 and/or an electromagnetic tracking system that can be included in the navigation system 10.

One or more changes in a pattern 110 of the tracking devices 108 can indicate to the navigation system 10 that a change in the instrument configuration has occurred. The change in the instrument configuration can include a change in an orientation of an instrument, addition or removal of a component to/from the instrument that can change the architecture of the instrument, a change to another instrument and/or some change in a medical setting that the medical professional or other suitable user wishes to communicate to the navigation system 10.

In one example, the tracking device holder member 102 can have a first arm portion 112 and a second arm portion 114. The first arm portion 112 can be shorter than the second arm portion 114 and can laterally extend in a direction that is away from the second arm portion 114. The first arm portion 112 and/or the second arm portion 114 can have an arcuate shape, such that the first and/or the second arm portions 112, 114 can also extend toward one another. In addition, the first arm portion 112 and the second arm portion 114 can lie in a plane that can be parallel to a plane 116.

The first arm portion 112 can include at least one of the posts 106 or other attachment device onto which one or more of the tracking devices 108 can be attached. The second arm portion 114 can include two posts 106 onto which one or more of the tracking devices 108 can be attached. In one example, one of the posts 106 onto which one of the tracking devices 108 can be attached can extend from the first arm portion 112 and two of the posts 106 can extend from the second arm portion 114. Each one of the posts 106 can have one of the tracking devices 108 attached thereto.

It will be appreciated in light of the disclosure that the amount of arm portions and any amount of tracking devices 108 on each of the arm portions can be implemented in various combinations but still provide the one or more changes in the pattern 110 to indicate the change in the instrument configuration. The change in the instrument configuration can define one or more of the following: moving the multi-configuration tracking array 100 between a first medical instrument (e.g., the instrument 42, 42a, 42b) and a second medical instrument, changing an orientation of the medical instrument, adding or removing a component from the medical instrument, etc., as further described herein. Moreover, the arcuate shape of one or more of the arm portions 112, 114 can be configured such that the arm portions 112, 114 are sufficiently spaced from the instrument holder member 104 of the multi-configuration tracking array 100 so as to provide sufficient optical spacing so the optical tracking system 38 of the navigation system 10 can detect the tracking devices 108.

Figure 4:
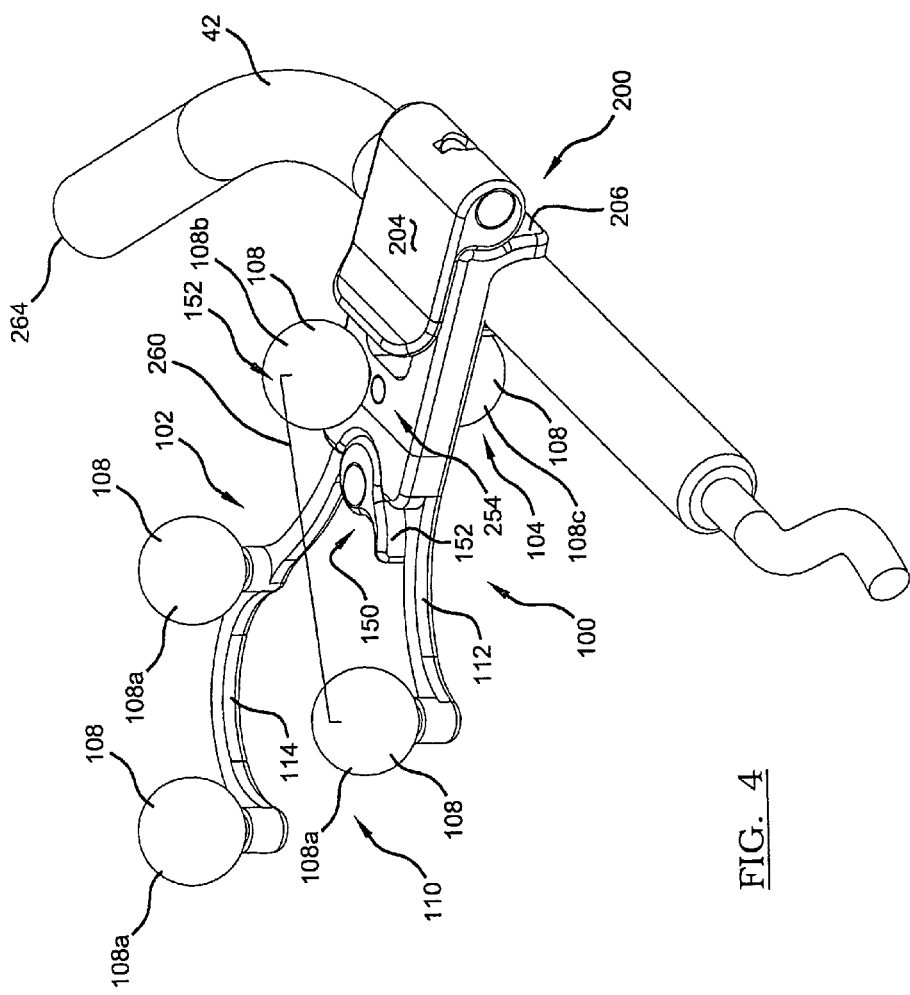
FIG. 4 is similar to FIG. 2 and shows the instrument holder member coupled to a first exemplary instrument and the tracking device holder member in a first position in accordance with the present teachings.
Figure 5:
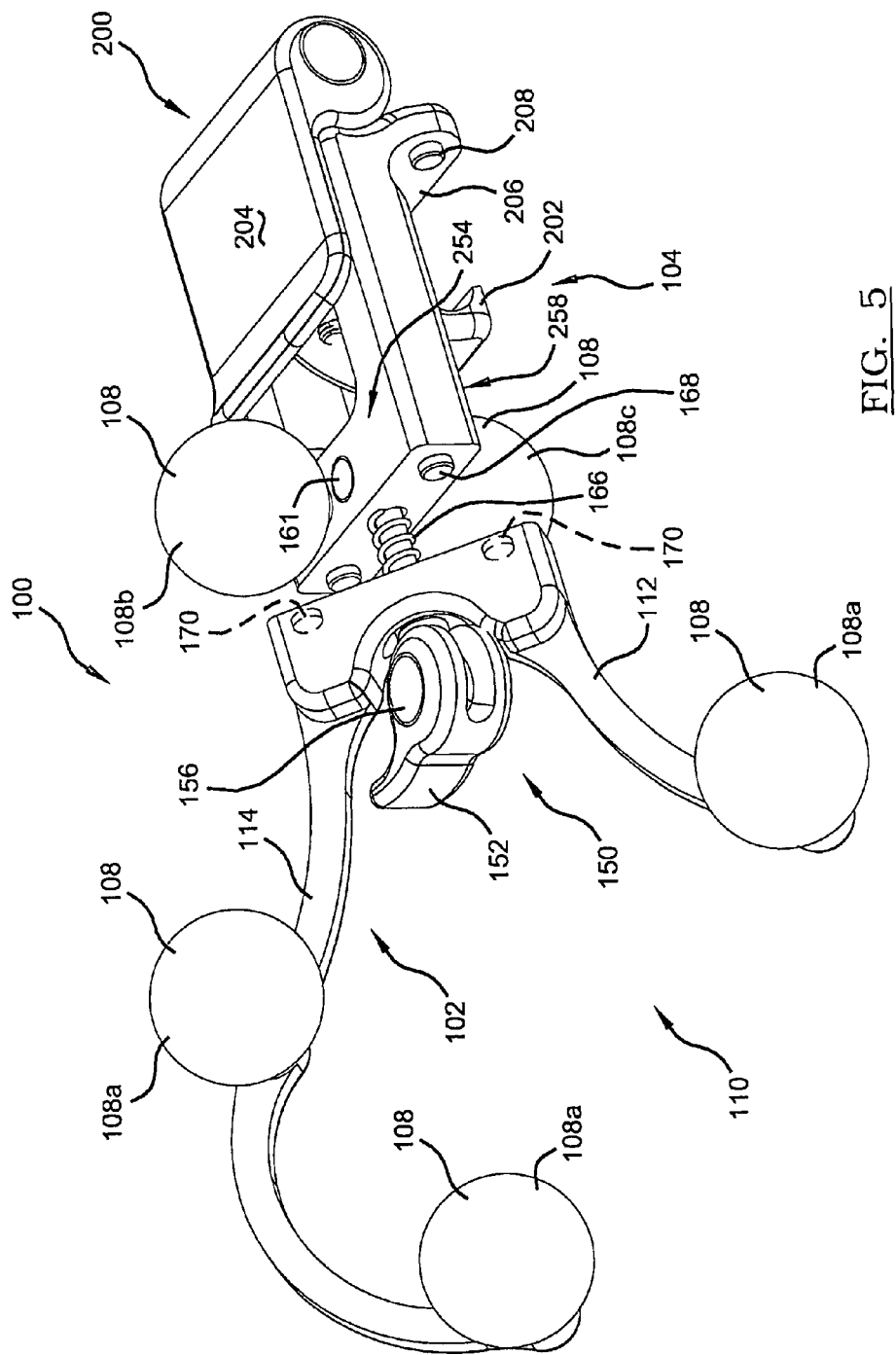
FIG. 5 is similar to FIG. 2 and shows the tracking device holder member in a position that is between the first condition and a second condition in accordance with the present teachings.

A lock assembly 150 can have a lock condition (FIG. 4) and a release condition (FIG. 5). The lock assembly 150 can be coupled to the tracking device holder member 102 and can releasably secure the tracking device holder member 102 to the instrument holder member 104. The lock assembly 150 can include a handle 152 that can rotate about a fastener 154 that can be partially contained within the handle 152 with a nut 156. The fastener 154 can extend from the nut 156 through an aperture 158 defined in a body portion 160 of the tracking device holder member 102 from which the arm portions 112, 114 extend. The fastener 154 can be secured to a nut 161 contained in an aperture 162 formed in a body portion 164 of the instrument holder member 104.

Figure 6:
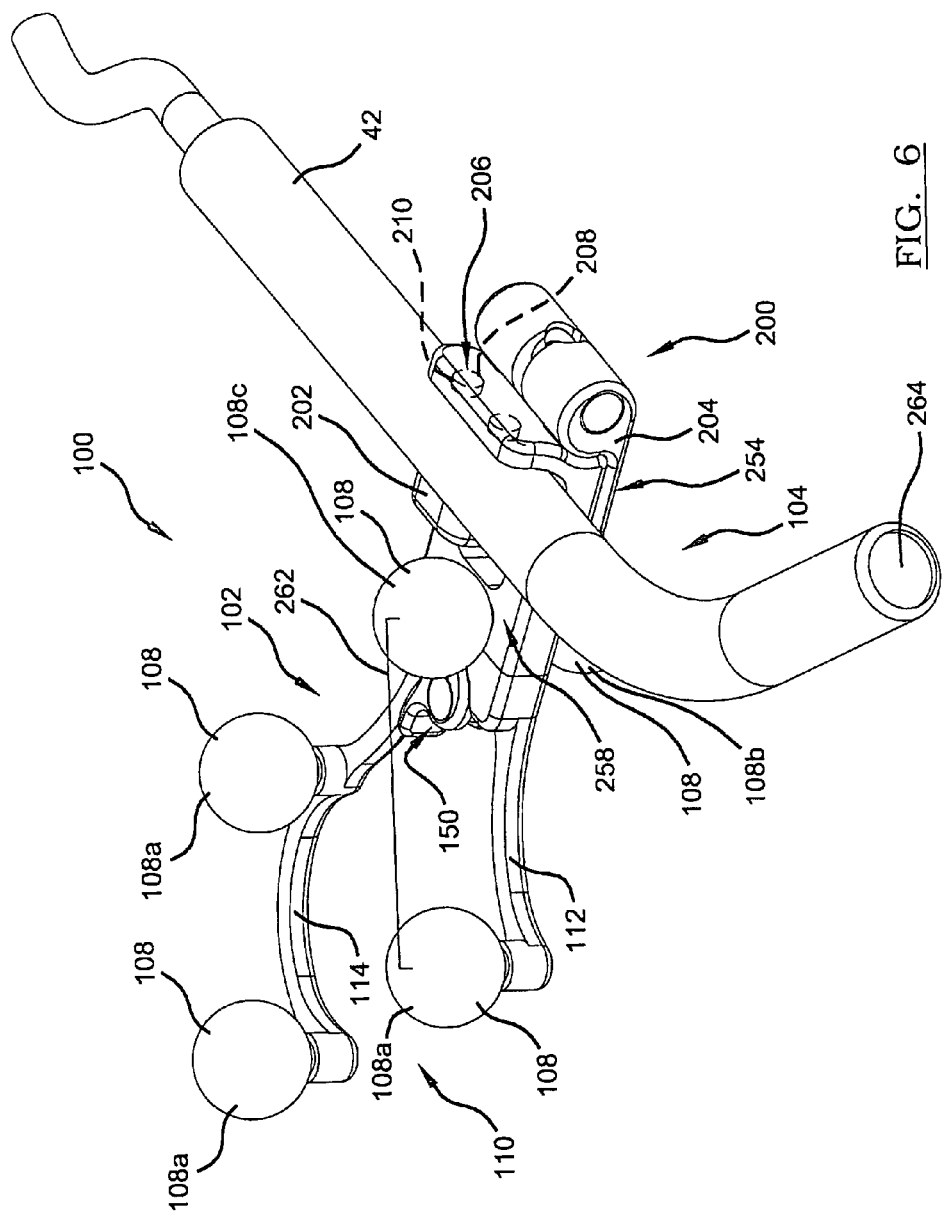
FIG. 6 is similar to FIG. 2 and shows the tracking device holder member in a second position in accordance with the present teachings.

The handle 152 can be rotated to place the lock assembly 150 in the release condition and thus partially release the tracking device holder member 102 from the instrument holder member 104, as shown in FIG. 5. In this regard, the tracking device holder member 102 can move relative to (e.g., pivot about) the instrument holder member 104. The tracking device holder member 102 can be moved relative to the instrument holder member 104 between a first position (FIG. 4) and a second position (FIG. 6). In one example, a portion of the handle 152 can have an asymmetric thickness that can cause the tracking device holder portion 102 to be urged toward the instrument holder member 104 as the handle 152 is moved between the lock condition (FIG. 2) and the release condition (FIG. 5).

With reference to FIG. 3, a spring 166 can be disposed between the instrument holder member 104 and the tracking device holder member 102. The spring 166 can be in a compressed condition when the lock assembly 150 holds tracking device holder member 102 in a lock condition (FIG. 2) and thus fixed to the instrument holder member 104. As shown in FIG. 5, the spring 166 can be in an uncompressed or less compressed condition when the tracking device holder member 102 is in an unlock condition, i.e., able to move relative to the instrument holder member 104. When the tracking device holder member 102 is in either the first position (FIG. 4) or the second position (FIG. 6), the lock assembly 150 in the lock condition (FIG. 2) can hold the tracking device holder member 102 to the instrument holder member 104 as one single rigid unit.

With reference to FIG. 5, one or more protrusions 168 can extend from the instrument holder member 104 and can be received respectively by one or more apertures 170 formed in the tracking device holder member 102. It will be appreciated in light of the disclosure that the one or more protrusions 168 can extend from the tracking device holder member 102 and can be received by respective apertures 170 formed in the instrument holder member 104. The combination of the protrusions 168 and the apertures 170 can further secure the tracking device holder member 102 in either the first or the second positions, as shown in FIGS. 4 and 6, respectively.

With reference to FIG. 5, when the lock assembly 150 is moved to the release condition, the tracking device holder member 102 can be moved in a direction away (i.e., generally leftward as illustrated in FIG. 5) from the instrument holder member 104. The tracking device holder member 102 can be moved a sufficient distance to clear the one or more protrusions 168 that extend from either the tracking device holder member 102 or the instrument holder member 104. As such, the tracking device holder member 102 can be permitted to rotate relative to the instrument holder member 104 between the first and second positions (FIGS. 4 and 6, respectively).

Once the tracking device holder member 102 is rotated to one of the first or second positions, the lock assembly 150 can be moved to the lock condition. By doing so, the handle 152 can drive the tracking device holder member 102 toward the instrument holder member 104 and can drive the protrusions 168 into the apertures 170 to lock the tracking device holder member 102 to the instrument holder member 104. Once locked in either the first position or the second position, the tracking device holder member 102 can be rigidly locked to the instrument holder member 104.

Each of the posts 106 on the one or more arm portions 112, 114 of the tracking device holder member 102 can be configured to releasably couple to the tracking devices 108. The tracking devices 108 and/or one or more components or portions of the multi-configuration tracking array 100 can be configured to be and/or made of suitable materials that can be sterilized, discarded after a single use and/or one or more applicable combinations thereof. Each of the tracking devices 108 can have various configurations that allow the navigation system 10 via the optical tracking system 38 (FIG. 1) to see and identify each of the tracking devices 108 and/or a change in each of the positions thereof.

In one example, the tracking devices 108 can each define a generally spherical shape that can be reflective to waves in the infrared range. For example, an infrared signal can be produced by the optical tracking system 38 and can be reflected off of the tracking devices 108 and thus returned to the optical tracking system 38. In another example, the tracking devices 108 can be releasably coupled to the tracking device holder member 102 and can be disposed of after use.

With reference to FIGS. 3 and 4, the instrument holder member 104 can include a lever assembly 200 that can be connected to the body portion 164 of the instrument holder member 104. The lever assembly 200 can include a catch member 202 that can move in response to motion of a handle 204. The catch member 202 can be disposed opposite a seat portion 206 formed in the body portion 164 (or formed as one or more separate components and suitably fixed thereto). Moving the handle 204 about a pin 205 from an unlocked condition to a locked condition can move the catch member 202 toward the seat portion 206 via a fastener 207 that can connect to a pin 209 that can be contained within the catch member 202. In the locked condition, the instrument holder member 104 can hold various suitable instruments (e.g., the instrument 42, 42a, 42b) between the seat portion 206 and the catch member 202. In one example, the lever assembly 200 can be omitted and the multi-configuration tracking array 100 can be integral to a specific instrument 42. In this example, the tracking device holder member 102 can be rotated relative to the instrument 42, but the multi-configuration tracking array 100 is permanently affixed (i.e., integral) to the medical instrument 42 or other suitable instrument.

In an example where the multi-configuration tracking array 100 is releasably connectable to the medical instrument 42 or other suitable medical instrument and with reference to FIG. 6, two reference keys 208 can extend from the seat portion 206. Each of the reference keys 208 can be received by apertures 210 formed on a predetermined reference location on the instrument 42. By connecting the multi-configuration tracking array 100 to the instrument 42 and seating the reference keys 208 in the respective apertures 210 on the instrument 42, the navigation system 10 can rely on the relative positions of the instrument 42 and the multi-configuration tracking array 100. In this regard, a resulting configuration of the combination of the multi-configuration tracking array 100 and the medical instrument 42 can be predetermined and thus known.

When the multi-configuration tracking array 100 is coupled to the instrument 42 so the reference keys 208 can be located in the respective apertures 210, the handle 204 of the lever assembly 200 can be moved from the unlocked condition to the locked condition. In doing so, the lever assembly 200 can draw the catch member 202 toward the seat portion 206 to secure the instrument 42 to the multi-configuration tracking array 100. As such, the tracking device holder member 102 can be unlocked and rotated relative to the instrument holder member 104 without the need for removing the multi-configuration tracking array 100 from the instrument 42. In this example, by changing the position of the tracking device holder member 102, i.e., rotating it about one hundred eighty degrees while attached to the same instrument 42, the change in the position of the tracking device holder member 102 can indicate a change in the configuration of the instrument 42. In a further example, switching the tracking device holder member 102 between the first position and the second position can indicate that the multi-configuration tracking array 100 has been mounted to a second (i.e., another) medical instrument.

In the various aspects of the present teachings, the change in the instrument configuration can be a change in the orientation of the instrument 42, as shown in FIGS. 4 and 6. For example, the change in the orientation of instrument 42 can include moving the instrument 42 from a right hand of a medical professional to a left hand of a medical professional such that the medical instrument is orientated in a different position. This can be important when the medical instrument has an asymmetric configuration such as the medical instrument shown in FIG. 4. Because the medical instrument can have an asymmetric configuration, moving the medical instrument to a different hand of a medical professional can, for example, re-orient a tip 264 of the instrument 42, e.g., a change position between the tip 264 in FIG. 4 and the tip 264 in FIG. 6.

In another example, a change in the instrument configuration can include connecting one or more components to the medical instrument to which the multi-configuration tracking array 100 is coupled. In this example, a camera, for example, can be added to the medical instrument 42. An end of the camera can extend from the medical instrument such that the end of the medical instrument is now at a different location than without the camera. In this instance, the change in the instrument configuration can be indicative of a change in the architecture of the medical instrument 42 due to the addition of the camera. As such, the navigation system 10 can recognize a new end of the instrument 42 and can display the new architecture in the image data.

In a further example, the change in the instrument configuration can include moving the multi-configuration tracking array 100 from a first medical instrument to a second medical instrument. In this example, the change between the first medical instrument and the second medical instrument need not be individually registered in the surgical navigation system 10 but can be indicated by changing the tracking device holder member from the first position to the second position.

In one example and with reference to FIG. 2, three of the tracking devices 108a attached to the tracking device holder member 102 and a fourth tracking device 108b can extend from the instrument holder member 104 on a first side 254 of the instrument holder member 104 (also see FIG. 2). A fifth tracking device 108c can extend from the instrument holder member 104 on a second side 258 that can be opposite of the first side 254. As the tracking device holder member 102 is rotated between the first and the second positions, the three tracking devices 108a on the tracking device holder member 102 can be in a different orientation relative to the fourth tracking device 108b when compared to the three tracking devices 108a positioned relative to the fifth tracking device 108c.

For example and with reference to FIGS. 4 and 6, a value can define a distance 260 (FIG. 4) from one or more of the three tracking devices 108a on the tracking device holder member 102 to the fourth tracking device 108b on the first side 254 of the instrument holder member 104. A second value can define a distance 262 (FIG. 6) from the one or more of the three tracking devices 108a relative to the fifth tracking device 108c on the second side 258 of the instrument holder member 104. A change in the pattern 110 of the tracking devices 108a, 108b, 108c can include the change between the first and the second values of the distances 260, 262 between the tracking devices 108. The change in the pattern 110 can indicate to the navigation system 10 that there has been a change of the instrument configuration.

Figure 7A:
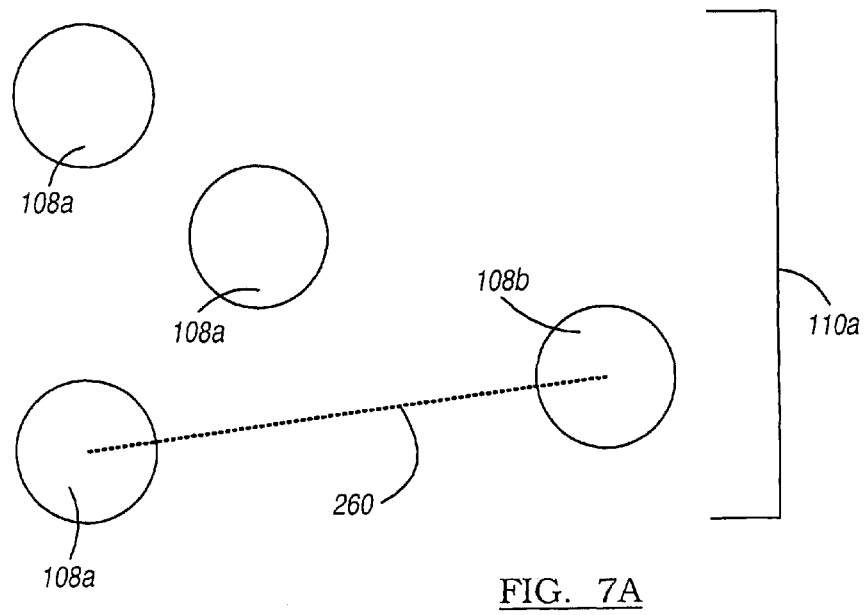
FIG. 7A is a diagram of the tracking devices associated with the multi-configuration tracking array in the first condition.
Figure 7B:
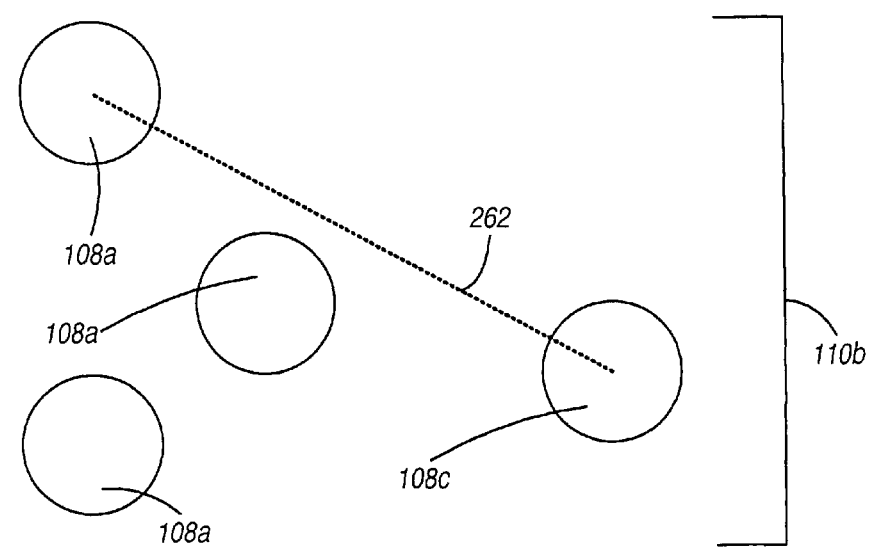
FIG. 7B is a diagram of the tracking devices associated with the multi-configuration tracking array in the second condition and a distance between the tracking devices changing relative to a pattern of the tracking device in FIG. 7A.

In a further example and with reference to FIGS. 7A and 7B, a change in the pattern 110 (FIG. 2) established by the tracking devices 108a, 108b, 108c is shown. In FIG. 7A, a first pattern 110a of the tracking devices 108a, 108b is shown and in FIG. 7B, a second pattern 110b of the tracking devices 108a, 108c is shown. Specifically, the pattern 110a can be a simplified representation of the three tracking devices 108a on the tracking device holder member 102 (FIG. 3) and the fourth tracking device 108b in the instrument holder member 104 with the tracking device holder member 102 in the first position. The pattern 110b can be a simplified representation of the three tracking devices 108a on the tracking device holder member 102 and the fifth tracking device 108c on the instrument holder member 104 with the tracking device holder member 102 in the second position. By changing between the first pattern 110a and the second pattern 110b, the change between the first distance 260 and the second distance 262 can be established.

Figure 8:
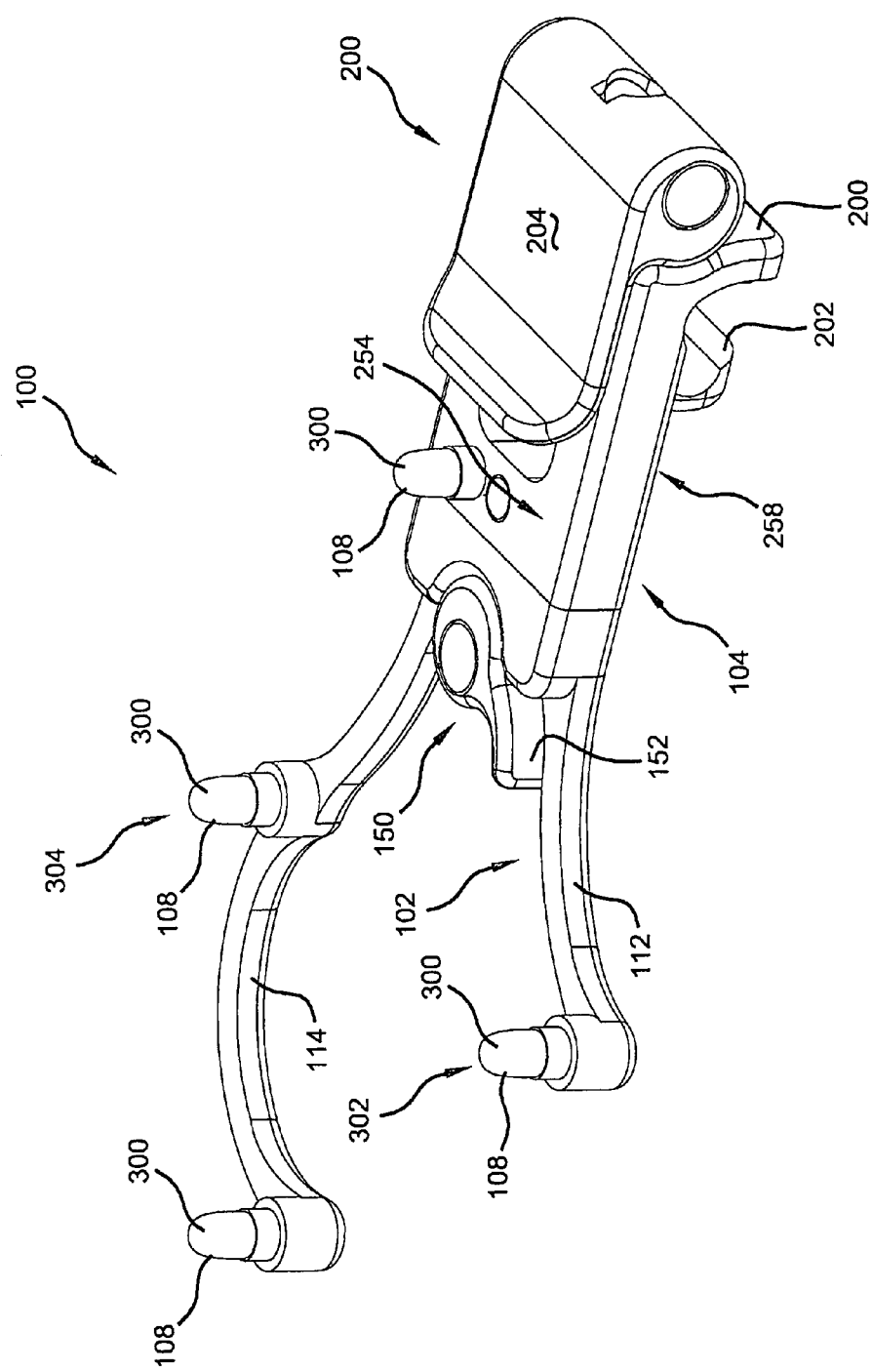
FIG. 8 is similar to FIG. 2 and shows each of the tracking devices configured as signal modules each capable of selectively emitting a light or other suitable electromagnetic signal in accordance with the present teachings.

In another aspect of the present teachings and with reference to FIG. 8, the one or more tracking devices 108 can each define a signal module 300 that can be connected to the tracking device holder member 102. The signal modules 300 can each emit light that can be received by the optical tracking system 38. The signal modules 300 can each define a light emitting diode that can each emit light at a predetermined frequency.

In one example, a first signal module 302 can be connected to the multi-configuration tracking array 100. In this example, a change in the signal emitted from the first signal module 302 can indicate a change in the instrument configuration. The change in the signal emitted from the first signal module 302 can be a change in the intensity of the light, a change in the color of the light, the light being on or off and/or one or more combinations thereof. In addition, the physical location of the tracking devices 108 can change (i.e., the LEDs can move) to indicate the change in the instrument configuration, e.g., a change between a first instrument configuration, a second instrument configuration, a third instrument configuration, a fourth instrument configuration, etc.

In other examples, two or more signal modules 300 can be connected to the multi-configuration tracking array 100 such that a change in one (or both) of the signals emitted from the respective signal modules 300 can indicate a change in the instrument configuration. In this example, the first signal module 302 can emit light (i.e., the LED is on) while a second signal module 304 does not emit any light (i.e., the LED is off). Following this same example, when light is emitted from both of the signal modules 302, 304 relative to just one of the signal modules 302, 304 the change in the light from the respective signal modules 302, 304 can indicate a change in the instrument configuration.

Figure 9:
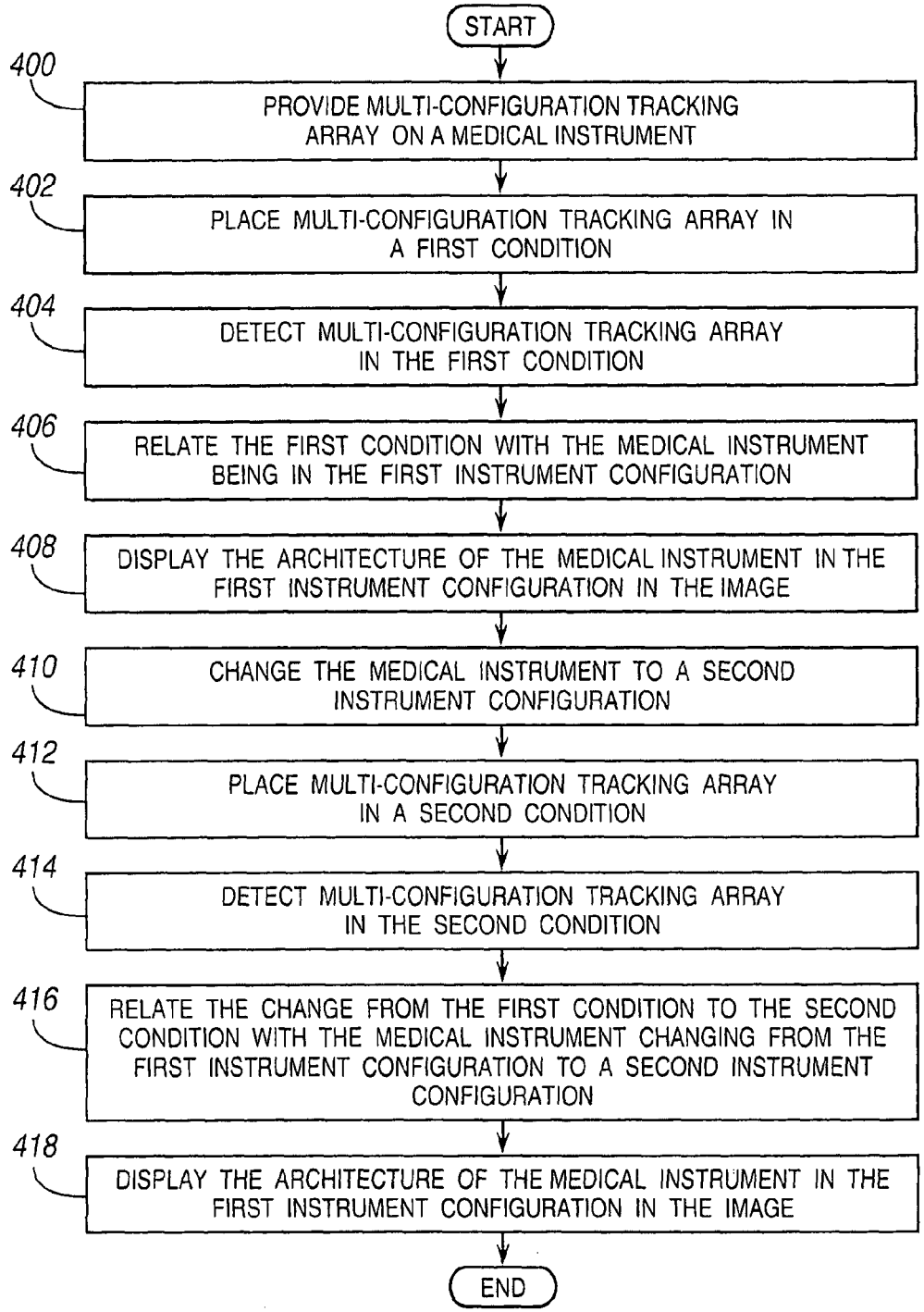
FIG. 9 is a flow chart of an exemplary operation of the multi-configuration tracking array switching between the first condition and the second condition to indicate a change between the first instrument configuration and the second instrument configuration in accordance with the present teachings.

In a further aspect of the present teachings and with reference to FIG. 8, the one or more tracking devices 108 can each define the signal module 300 that can be connected to the tracking device holder member 102. The signal modules 300 can each emit an electromagnetic signal that can be received by a suitable electromagnetic tracking system. The signal modules 300 can each define one or more coils that can selectively establish an electric field that can be detected. As such, a change in the electric field can be indicative of the change between the first instrument configuration and the second instrument configuration, etc. It will be appreciated in light of the disclosure that the coils can change relative to one another to indicate the change between the first instrument configuration and the second instrument configuration. In addition, the coil positions can change field intensity, the field orientation and/or other field properties to indicate the change between the first instrument configuration and the second instrument configuration In operation and with reference to FIG. 9, the multi-configuration tracking array 100 (FIG. 3) can be implemented with a medical instrument that can, for example, be a probe that can accept a camera. The architecture of the probe and the camera can be registered with the navigation system 10 (FIG. 1). In 400, the multi-configuration tracking array 100 can be provided on the probe or other suitable medical instrument. In 402, the multi-configuration tracking array 100 can be placed in the first condition, e.g., the first position as shown in FIG. 3. In 404, the optical tracking system 38 (FIG. 1) can detect the multi-configuration tracking array 100 in the first condition.

In 406, the surgical navigation system 10 can relate the detection of the multi-configuration tracking array 100 in the first condition with architecture of the probe, so that a portion of the probe can be located as the probe is moved relative to the patient 12 during a suitable image-guided surgical navigation procedure. In this example, the architecture of the probe without the camera can define the first instrument configuration. In 408, the navigation system 10 can display the architecture of the first instrument in the first instrument configuration or other suitable instrument configuration.

In 410, the probe can accept the camera so that a portion of the camera can extend from the probe. It will be appreciated in light of the disclosure that including the camera with the probe changes the architecture of the instrument so that the medical instrument has changed from a first configuration (i.e., probe only) to a second configuration (i.e., probe and camera). In 412, the multi-configuration tracking array 100 is changed from the first condition to the second condition. In 414, the optical tracking system 38 can detect the change from the first condition to the second condition of the multi-configuration tracking array 100.

In 416, the navigation system 10 can relate the change in the multi-configuration tracking array 100, i.e., the change from the first condition to the second condition, to the change from the first instrument configuration to the second instrument configuration, etc., i.e., the addition of the camera. In 418, the navigation system 10 can display the architecture of the first instrument in the second instrument configuration. In this regard and with reference to FIG. 10, an icon 500 can be displayed on a display 502 that also shows image data 504 (e.g., a portion of the patient anatomy). The icon 500 can move relative to the image data 504 as an instrument 42 to which the multi-configuration tracking array 100 is attached and moves relative to the patient anatomy imaged in the image data 504. The icon 500 on the display can change to represent the new configuration, e.g., the architecture of the first instrument in the second instrument configuration or other suitable configuration, as discussed with reference to 418 in FIG. 9. In this example, the camera or tip extends further out from the instrument and the icon 500 can change to represent this change.

In other aspects of the present teachings, the icon 500 can change to indicate the change between the first condition and the second condition of the multi-configuration tracking array that indicates a change between the first instrument configuration, the second instrument configuration, the third instrument configuration, the fourth instrument configuration, etc. For example and with reference to FIG. 10, an icon 506 can represent an asymmetric probe. The icon 506 can change from a first condition 508 to a second condition 510 that can indicate that the probe has changed orientations, possibly due to a medical professional changing the probe to another hand. By changing the multi-configuration tracking array 100 from the first condition to the second condition, the icon 506 can change to indicate the change between the first instrument configuration and the second instrument configuration of the probe. It will be appreciated in light of the disclosure, the icon 500, 506, etc. can change to visibly show the change of the architecture and/or orientation of the tool, probe, etc. or can change in other ways to indicate the same.

Other examples can include various changes in the orientation of the instrument, connecting one or more additional components to the instrument, moving the multi-configuration tracking array 100 from a first medical instrument to a second medical instrument. Further examples can include an icon 512 that represents an awl/tap/probe and a drill that can extend from the probe, such that the drill bit establishes a tip 514 of the probe. The multi-configuration tracking array can be changed from the first condition to the second condition to indicate the addition of the drill bit that establishes a new tip 516 for the probe. Another example includes an implant inserter such that the icon can change to indicate when the implant is attached to the inserter. Further examples include an icon that can change to indicate: a change in drill speed, a departure from an intended drill speed, a change in a drilling depth, achieving a predetermined drilling depth and/or one or more combinations thereof.

According to various aspects of the present teachings and with reference to FIG. 11, any one of the instruments 42 can include, for example, a multi-tip instrument 42c. The multi-tip instrument 42c can include a handle portion 600 and various tip portions. Examples of tip portions can include an awl 602, a tap 604, and a probe 606. The various tips 602, 604, 606 can interconnect with the handle portion 600 that extends from an interconnection portion 608. The interconnection portion 608 can interconnect with connection portions associated with the various tips 602, 604, 606, i.e., an awl connection portion 610, a tap connection portion 612, and a probe connection portion 614. The connection portions can include any suitable connection, such as a quick connect, a twist lock, a snap-fit, or the like.

The various tips 602, 604, 606 can each include an engagement or keyed portion 628, 630, 632 on the awl 602, the tap 604, and the probe 606, respectively. The engagement or keyed portions 628, 630, 632 can engage a keyed portion on the connection portion 608. This arrangement can insure that the tip portion 602, 604, 606 is oriented in an appropriate selected manner with the handle portion 600. The connection of the keyed portions 628, 630, 632 of the respective tips 602 604, 606 to the handle portion 600 at the connection portion 608 can communicate to the tracking system 38 (FIG. 1) that a new tip 602, 604, 606 has been connected to the handle portion 600. With this communication, the tracking system 38 can detect tracking devices 650, 652, 654 on the handle portion 600 and tracking devices 656, 658, 660 on the tips 602, 604, 606 respectively. It will also be appreciated in light of the disclosure that any appropriate number of tips can be provided. For example, the probe 606 can be provided in a plurality of lengths, configurations, sizes or the like. Also, the tap 604 can also be provided in various sizes for different users. Also, different instruments not specifically illustrated can be provided to interconnect with the handle portion 600.

The handle portion 600 can include the three tracking devices 650, 652, 654 that can each extend from the handle 600 with respective arms 662. When one of the tips 602, 604, 606 is connected to the handle 600 via the connection portion 608, a pattern (see, e.g., FIGS. 7A and 7B) can be established to identify which of the tips have been connected to the handle. In one example, the tracking devices 656, 658, 660 can establish varying patterns when associated with the tracking devices 650, 652, 654 on the handle portion 600 because of the relative differences in the distances of the tracking devices 656, 658, 660 from the tracking devices 650, 652, 654 associated with the handle portion 600. It will be appreciated in light of the disclosure that while a single tracking device (e.g., tracking devices 656, 658, 660) is associated with each tip portion 602, 604, 606, two or more tracking devices can be associated with each of the tip portions 602, 604, 606 to establish a pattern that is indicative of the respective tip portion. Moreover, one tip portion can have one tracking device, while another tip portion can have two or more tracking devices to establish a pattern with the tracking devices 650, 652, 654 on the handle portion 600. Further, the handle portion 600 can also have additional tracking devices.

The tracking system 38 (FIG. 1) can detect the pattern established by the tracking devices 650, 652, 654 and one of the tracking devices 656, 658, 660 when the respective keyed portions 628, 630, 632 of the tips 602, 604, 606 connect to the handle portion 600 and communicate with the imaging system 38. In this regard, the connection of tips 602, 604, 606 to the connection portion 608 can, for example, start a detection period in which the imaging system looks for a change in a pattern established by the applicable tracking devices 650, 652, 654, 656, 658, 660. In a further example, the mere change in the pattern established by the applicable tracking devices 650, 652, 654, 656, 658, 660 (or additional tracking devices) can serve to trigger the detection of one of the tips 602, 604, 606 attached to the handle portion 600 and thus the need to use the keyed portions 628, 630, 632 with the connection portion 608 can be avoided.

Relative to the tracking devices 650, 652, 654 on the handle portion 600, the tracking devices 656, 658, 660 (or additional tracking devices) on the tip portions 602, 604 606 respectively, can be at predetermined distances relative to each and from the handle portion 600. For example, the tracking device 660 on the tip 606 can be at a first distance increment 664 from the tracking device 658 on the tip 604. Moreover, the tracking device 658 on the tip 604 can be at a second distance increment 666 from the tracking device 656 on the tip 602. Further, each of the tracking devices 656, 658, 660 can be at a given distance from the tracking devices 650, 652, 654 when installed on the handle portion 600. The connection of the tips 602, 604, 606 to the handle portion 600 can be communicated to the imaging system 38 via a wireless 672 or a wired communication system 670.

As discussed above, the connection of one of the tip portions 602, 604 606 relative to a different tip portion to the handle portion 600 can be akin to changing the multi-configuration tracking array 100 between a first condition (see, e.g., FIG. 4) and a second condition (see, e.g., FIG. 6), which is indicative of a change between a first tool configuration and a second tool configuration. The first tool configuration can be in this example, one of the tip portions 602, 604, 606, while the second tool configuration can be change to a second tip, e.g., awl 602 to probe 606. The first condition, for example, can be a pattern established by tracking devices 650, 652, 654, 656, which the second condition can be a pattern established by the tracking devices 650, 652, 654, 660. Upon detection of the change of the pattern of tracking devices, i.e., a change from the first condition to the second condition, the navigation system 10 can display the architecture of the applicable tip portion 602, 604, 606 associated with the handle portion 600. As similarly discussed in 418 in FIG. 9, the icon 500 as shown in FIG. 10 on the display 502 can show the applicable tip portion 602, 604, 606 and its configuration as attached to the handle portion 600 relative to the patient's anatomy 504 (FIG. 10).

In accordance with the various aspects of the present teachings, the tracking devices 650, 652, 654, 656, 658, 660 can communicate (actively and/or passively) with the optical tracking system 38 and/or an electromagnetic tracking system that can be included in the navigation system 10. As such, the tracking devices 650, 652, 654, 656, 658, 660 can include various tracking sensors, such as electromagnetic coils or optical detection points, such as light emitting diodes or reflectors that may be detected by a suitable tracking system.

While specific aspects have been described in this specification and illustrated in the drawings, it will be appreciated in light of the disclosure that various changes can be made and equivalents can be substituted for elements thereof without departing from the scope of the present teachings, as defined in the Claims. Furthermore, the mixing and matching of features, elements and/or functions between various aspects of the present teachings can be expressly contemplated herein so that one skilled in the art will appreciate from the present teachings that features, elements and/or functions of one aspect of the present teachings can be incorporated into another aspect, as appropriate, unless described otherwise above. Moreover, many modifications can be made to adapt a particular situation, configuration or material to the present teachings without departing from the essential scope thereof. Therefore, it can be intended that the present teachings not be limited to the particular aspects illustrated by the drawings and described in the specification as the best mode presently contemplated for carrying out the present teachings but that the scope of the present teachings will include many aspects and examples following within the foregoing description and the appended claims.

What is claimed is:

1. A method of performing a procedure with a first instrument so that a configuration of the first instrument is included in a view produced from a surgical navigation process used to perform the procedure, the method comprising:
   detecting a location in a first configuration relative to each other of at least a first tracking emitter with a medical instrument holder and at least three second tracking emitters defining a plane with a tracking device holder;
   changing a pattern of said first and second tracking emitters;
   detecting said changed pattern of said first and second tracking emitters; and
   relating said changed pattern of said first and second tracking emitters with a change between a first instrument configuration and a second instrument configuration, wherein changing a pattern of said first and second tracking emitters includes switching a first signal module between a first condition and a second condition and wherein said change between said first condition and said second condition comprises:
      emitting light and not emitting light from at least one of said first and second tracking emitters while maintaining the first configuration relative to each other.

2. The method of claim 1 wherein said changing of said pattern of said first and second tracking emitters includes rotating the tracking device holder with respect to the medical instrument holder.

3. The method of claim 1 wherein said change between said first instrument configuration and said second instrument configuration includes at least a change in an orientation of the first instrument relative to the patient.

4. The method of claim 1 wherein said change between said first instrument configuration and said second instrument configuration includes at least coupling or uncoupling a component to the first instrument.

5. The method of claim 1 wherein said change between said first instrument configuration and said second instrument configuration includes at least uncoupling said tracking apparatus from the first instrument and coupling said tracking apparatus to a second instrument that is different than the first instrument.

6. The method of claim 1 further comprising acquiring image data with an imaging system from a patient, said image data collected at least one of pre-operatively, intra-operatively, or post-operatively.

7. The method of claim 1 further comprising obtaining data with a system, said data based on at least one of atlas models, patient specific atlas models, previous images obtained with an imaging system and one or more combinations thereof.

8. The method of claim 6 further comprising:
   displaying a first icon over said image data, said first icon indicative of said first instrument configuration;
   automatically changing from said first icon to a second icon based on said changing of at least one of said signal or pattern of said first and second tracking devices; and
   displaying said second icon over said image data, wherein said second icon reflects said change between said first instrument configuration and a second instrument configuration so that said second icon at least partially represents said second instrument configuration.

9. The method of claim 8 wherein automatically changing from said first icon to said second icon indicates at least one of:
   a camera extending from a tip of the first medical instrument such that said camera established a new tip of the first medical instrument,
   changing an orientation of the first medical instrument that defines an asymmetric probe,
   connecting one or more additional components to the first medical instrument,
   a drill bit extending from an awl/tap/probe such that the drill bit establishes a new tip of the probe,
   an implant attached to an implant inserter,
   a change in drill speed of a drill associated with the first medical instrument, and
   one or more combinations thereof.

10. The method of claim 1 further comprising rotating a body having an asymmetric thickness from a first unlocked position to a second locked position to selectively lock the position of the first and second tracking devices by selectively urging the first and second tracking devices together.

11. The method according to claim 1 wherein the first tracking emitter and second tracking emitters define a first detectable pattern in the first condition and the first tracking device and second tracking devices define a second detectable pattern in the second condition.

12. The method of claim 8 wherein said change between said first condition and said second condition further comprises:
   changing an intensity of light from at least one of said first and second tracking emitters.

13. The method of claim 12 wherein said change between said first condition and said second condition further comprises:
   one or more combinations of changing an intensity of light from at least one of said first and second tracking emitters, or
   emitting light and not emitting light from at least one of said first and second tracking emitters while maintaining the first configuration relative to each other.

14. The method of claim 8 wherein said change between said first condition and said second condition further comprises:
   changing a color of light from at least one of said first and second tracking emitters.

15. A method of performing a procedure with a first instrument and a second instrument so that a configuration of the first instrument and the second instrument are included with a view produced from a surgical navigation process, the method comprising:
   detecting a first tracking device and a second tracking device on a tracking apparatus having a tracking device holder member with said first tracking device and an instrument holder member with said second tracking device, said instrument holder member removably coupled to the first instrument, such that said instrument holder member is operable to be connected separately to both the first instrument and the second instrument;
   operating at least one tracking emitter of at least one of said first tracking device or said second tracking device to emit light to generate a first pattern or not emit light to generate a second pattern different than the first pattern; and detecting the first pattern or the second pattern of light emitted from said first tracking device and second tracking device.

16. The method of claim 15, further comprising:
providing the first tracking device to define a detectable plane.

17. The method of claim 16, further comprising:
movably coupling the tracking device holder member to the instrument holder member.

18. The method of claim 15 wherein operating at least one tracking emitter of at least one of said first tracking device or said second tracking device to emit light to generate said first pattern or not emit light to generate said second pattern different than the first pattern includes at least a change in an orientation of the first instrument relative to a patient.

19. The method of claim 15 wherein operating at least one tracking emitter of at least one of said first tracking device or said second tracking device to emit light to generate said first pattern or not emit light to generate said second pattern different than the first pattern includes at least coupling or uncoupling a component to the first instrument.

20. The method of claim 15 wherein operating at least one tracking emitter of at least one of said first tracking device or said second tracking device to emit light to generate said first pattern or not emit light to generate said second pattern different than the first pattern is based on a connection to the first instrument or connection to the second instrument.

21. A method of selecting a view of a first instrument so that a configuration of the first instrument is included in a view produced from a surgical navigation system, the method comprising:
selecting at least one of a first medical instrument tip with a connected first tracking device or a second medical instrument tip with a connected second tracking device;
connecting said selected first medical instrument tip or said second medical instrument tip to a device holder having a connected third tracking device;
operating the surgical navigation system to determine a first pattern or a second pattern including a relative location of said connected third tracking device and at least one of said first tracking device or said second tracking device; and
operating the surgical navigation system to determine the identification of the selected first instrument tip or the second instrument tip for producing the view.

22. The method of claim 21, further comprising:
selecting the other of the first instrument tip or the second instrument tip;
connecting the selected other of the first instrument tip or the second instrument tip to change from the first pattern to the second pattern of said first tracking device or said second tracking device relative to said connected third tracking device;
detecting said change from the first pattern to the second pattern; and
relating said change from the first pattern to the second pattern with a change between the first instrument tip and the second instrument tip.

23. The method of claim 22, wherein change from the first pattern to the second pattern of said first tracking device or said second tracking device relative to said connected third tracking device includes switching a first signal module between a first condition and a second condition.

24. The method of claim 21, further comprising:
selecting all of the said first tracking device, said second tracking device, and said connected third tracking device to be optical tracking devices.

25. The method of claim 21, further comprising:
selecting said first medical instrument tip with a first connection portion, wherein said first tracking device is a first distance from said first connection portion; and
selecting said second medical instrument tip with a second connection portion, wherein said second tracking device is a second distance from said second connection portion and said second distance is different than the first distance;
wherein connecting said selected first medical instrument tip or said second medical instrument tip to said device holder includes connecting said selected first medical instrument tip at said first connection portion to said device holder or connecting said second medical instrument tip to said device holder at said second connection portion.

26. The method of claim 22, wherein operating the surgical navigation system to determine the identification of said selected first instrument tip or said second instrument tip includes operating the surgical navigation system to identify a first pattern of said first tracking device and said connected third tracking device or a second pattern of said second tracking device and said connected third tracking device;
wherein said first pattern is different from said second pattern.

27. The method of claim 26, wherein said connected third tracking device includes a plurality of third tracking devices; wherein said plurality of third tracking devices are fixed relative to one another.

28. The method of claim 21, further comprising:
engaging a first keyed portion of said first medical instrument tip or a second keyed portion of said second medical instrument tip with said device holder to communicate with the surgical navigation system.

29. The method of claim 28, wherein operating the surgical navigation system to determine the identification of said selected first instrument tip or said second instrument tip is automatic in response to said communication with the surgical navigation system.

30. The method of claim 22, wherein operating the surgical navigation system to determine the identification of said selected first instrument tip or said second instrument tip is automatic in response to detecting said changed pattern.

31. A method of producing a view from a surgical navigation system, the method comprising:
selecting at least one of a first medical instrument tip with a connected first tracking device or a second medical instrument tip with a connected second tracking device;
selecting a device holder having a connected at least one third tracking device;
connecting said selected first medical instrument tip or said second medical instrument tip to said selected device holder to form a first pattern of said connected first tracking device and said at least one third tracking device or a second pattern of said second tracking device and said at least one third tracking device;
operating the surgical navigation system to detect said first pattern or said second pattern, wherein said first pattern is different from said second pattern;
operating the surgical navigation system to determine an identification of a feature of said first medical instrument tip or said second medical instrument tip based on said operation of the surgical navigation system to detect said first pattern or said second pattern; and operating the surgical navigation system to display the determined feature.

32. The method of claim 31, further comprising:
changing from said first pattern to said second pattern by disconnecting said first medical instrument tip from said device holder and connecting said second medical instrument tip to said device holder;
wherein said operating the surgical navigation system to detect said first pattern or said second pattern is automatic when said change occurs.

33. The method of claim 31, further comprising:
changing from said second pattern to said first pattern by disconnecting said second medical instrument tip from said device holder and connecting said first medical instrument tip to said device holder;
wherein said operating the surgical navigation system to detect said first pattern or said second pattern is automatic when said change occurs.

34. The method of claim 31, further comprising:
engaging a first keyed portion of said first medical instrument tip or a second keyed portion of said second medical instrument tip to said device holder;
wherein said operating the surgical navigation system to detect said first pattern or said second pattern is automatic when said first keyed portion or said second keyed portion is engaged.

35. The method of claim 31, further comprising:
selecting all of said connected first tracking device, said connected second tracking device, said connected at least one third tracking device to be electromagnetic tracking devices.

36. The method of claim 31, wherein the first pattern and the second pattern differ by at least a distance of said connected first tracking device and said connected second tracking device relative to said connected at least one third tracking device.

37. A navigation system that determines a location of a portion of a first medical instrument relative to a patient, the navigation system comprising:
a tracking apparatus having at least one first tracking device connected thereto;
a device holder having a tip connection portion, wherein the tracking apparatus is connected to the device holder at a fixed position relative to the tip connection portion;
a first instrument tip having a first connection portion configured to connect to the tip connection portion of the device holder and a second tracking device connected to the first instrument tip a first distance from the first connection portion;
a second instrument tip having a second connection portion configured to connect to the tip connection portion of the device holder and a third tracking device connected to the second instrument tip a second distance from the second connection portion different than the first distance;
a tracking system configured to detect all of the at least one first tracking device, the second tracking device, and the third tracking device;
a surgical navigation system configured to identify a first feature of the first instrument tip when connected to the device holder based on a first pattern of the at least one first tracking device and the second tracking device and identify a second feature of the second instrument tip when connected to the device holder based on a second pattern of the at least one first tracking device and the third tracking device.

38. The system of claim 37, further comprising:
a display device configured to display a first icon representing the first feature or a second icon representing the second feature;
wherein the icon is based on a signal from the surgical navigation system after the identification.

39. The system of claim 37, wherein the surgical navigation system automatically identifies the first feature or the second feature when a change between the first pattern and the second pattern is detected based on the tracking system detecting the at least one first tracking device and at least one of the second tracking device or the third tracking device.

40. The system of claim 39, wherein the at least one first tracking device, the second tracking device, and the third tracking device are emitters;
wherein the tracking system is configured to detect the emitters.

41. The system of claim 39, wherein the surgical navigation system relates a change between the first pattern and the second pattern with a change between at least the first instrument tip and the second instrument tip.

42. The system of claim 41, further comprising:
a first key portion extending from the first instrument tip;
a second key portion extending form the second instrument tip;
a key receiving portion near the tip connection portion of the device holder;
wherein either of the first key portion or the second key portion is selectively received in the key receiving portion whereupon the device holder transmits a signal to at least one of the tracking system or the surgical navigation system for at least one of detecting the first pattern or the second patter or identifying the first feature or the second feature.

43. The system of claim 39, wherein the tracking apparatus includes a plurality of emitters positioned relative to each other and configured to emit a first pattern at a first condition and the plurality of emitters configured to emit a second pattern at a second condition, said plurality of emitters being changeable between the first condition and the second condition and thereby emit one of the first pattern and second pattern, wherein the first pattern is different from the second pattern.

44. The system of claim 39, wherein identifying the first feature includes identifying the first instrument tip as at least one of a delivery system, a guide wire, an arthroscopic system, an orthopedic implant, a spinal implant, a deep brain stimulation probe, an awl, a tap, or a probe.

45. The system of claim 39, wherein identifying the second feature includes identifying the second instrument tip as at least one of a delivery system, a guide wire, an arthroscopic system, an orthopedic implant, a spinal implant, a deep brain stimulation probe, an awl, a tap, or a probe.

46. A navigation system that determines a location of a portion of at least a first medical instrument relative to a patient, the navigation system comprising:
a tracking apparatus having a tracking device holder portion moveable relative to a medical device holder portion, wherein the medical device holder portion is configured to be selectively coupled to the first medical instrument, the medical device holder portion having a seat wall configured to engage the first medical instrument when a catch member moves via a lever assembly to capture the first medical instrument between the catch and the seal wall;
a lock assembly operably connected to the tracking apparatus having a nut captured in a bore of a body of the tracking apparatus and a fastener extending through a spring from a lock handle, wherein the lock handle is configured to move from a locked position to compress the spring and fix the tracking device holder portion relative to the medical device holder portion and an unlocked position to decompress the spring to allow movement of the tracking device holder portion and the medical device holder portion;
a plurality of emitters connected to the tracking device holder, wherein the plurality of emitters are positioned relative to each other and configured to emit a first pattern at a first condition and to emit a second pattern at a second condition, said plurality of emitters being changeable between said first condition and said second condition and thereby emit one of the first and second pattern, wherein the first pattern is different from the second pattern; and
a tracking system that detects said plurality of emitters and relates a change between said first condition and said second condition with a change between at least a first instrument configuration and a second instrument configuration;
wherein the lock assembly is configured to unlock the tracking device holder portion relative to the medical device holder portion to allow the change from the first pattern to the second pattern and to lock the tracking device holder portion relative to the medical device holder portion to fix the first pattern or the second pattern.

47. The system of claim 46, wherein the first pattern is operable to differ from the second pattern by at least one of changing an intensity of light from one of the plurality of emitters at a change from the first condition to the second condition, changing a color of light from one of the plurality of emitters at a change from the first condition to the second condition, changing a pattern of light from one of the plurality of emitters at a change from the first condition to the second condition, and one or more combinations thereof.

48. The system of claim 46, wherein the change between the first instrument configuration and the second instrument configuration includes at least a change in an orientation of the first medical instrument relative to the tracking apparatus.

49. The system of claim 46, wherein the change between the first instrument configuration and the second instrument configuration includes at least coupling or uncoupling a component to the first medical instrument.

50. The system of claim 48, wherein the change between the first instrument configuration and the second instrument configuration includes at least uncoupling the tracking apparatus from the first medical instrument and coupling the tracking apparatus to a second medical instrument.

51. The system of claim 50, wherein the first medical instrument is selected from a group consisting of a delivery system, a guide wire, an arthroscopic system, an orthopedic implant, a spinal implant, a deep brain stimulation probe, an awl/tap/probe and one or more combinations thereof.

52. The system of claim 46, further comprising:
a display device configured to display a first icon of the first medical instrument in the first instrument configuration and a second icon of the first medical instrument in the second instrument configuration, when the first and second tracking devices change between the first condition and the second condition.

* * * * *